United States Patent
Fu et al.

(10) Patent No.: US 10,435,479 B2
(45) Date of Patent: Oct. 8, 2019

(54) CHEMICALLY-LOCKED BISPECIFIC ANTIBODIES

(71) Applicant: Sorrento Therapeutics, Inc., San Diego, CA (US)

(72) Inventors: Yanwen Fu, San Diego, CA (US); Gunnar F. Kaufmann, San Diego, CA (US); Bryan Jones, San Diego, CA (US); Raheleh Toughiri, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 1 day.

(21) Appl. No.: 15/310,214

(22) PCT Filed: May 10, 2015

(86) PCT No.: PCT/US2015/030054
§ 371 (c)(1),
(2) Date: Nov. 10, 2016

(87) PCT Pub. No.: WO2015/175357
PCT Pub. Date: Nov. 19, 2015

(65) Prior Publication Data
US 2017/0260291 A1    Sep. 14, 2017

Related U.S. Application Data

(60) Provisional application No. 61/991,508, filed on May 10, 2014.

(51) Int. Cl.
*C07K 16/46* (2006.01)
*C07K 16/28* (2006.01)
*C07K 16/30* (2006.01)

(52) U.S. Cl.
CPC ........ *C07K 16/468* (2013.01); *C07K 16/2827* (2013.01); *C07K 16/2863* (2013.01);
(Continued)

(58) Field of Classification Search
None
See application file for complete search history.

(56) References Cited

U.S. PATENT DOCUMENTS

| 5,185,433 A | 2/1993 | Dean et al. |
| 2010/0105874 A1 | 4/2010 | Schuurman et al. |

(Continued)

FOREIGN PATENT DOCUMENTS

| WO | 2005/062916 A2 | 7/2005 |
| WO | 2010099273 A1 | 9/2010 |

(Continued)

OTHER PUBLICATIONS

Kim, C.H. et al. "Synthesis of Bispecific Antibodies using Genetically Encoded Unnatural Amino Acids," J Am Chem Soc, May 26, 2012, vol. 134: 9918-9921.

(Continued)

*Primary Examiner* — Karl J Puttlitz
(74) *Attorney, Agent, or Firm* — McNeill Baur PLLC

(57) ABSTRACT

There is disclosed a process for forming chemically-locked bispecific or heterodimer antibodies, preferably in the IgG class, in high specificity and with high homogeneity. More specifically, there is disclosed a chemically-locked bispecific IgG class antibody having a linkage region joined together with bio-orthogonal click chemistry.

9 Claims, 18 Drawing Sheets
Specification includes a Sequence Listing.

(52) U.S. Cl.
CPC .......... *C07K 16/30* (2013.01); *C07K 16/3015* (2013.01); *C07K 2317/31* (2013.01); *C07K 2317/51* (2013.01); *C07K 2317/515* (2013.01); *C07K 2317/53* (2013.01); *C07K 2317/54* (2013.01); *C07K 2317/55* (2013.01); *C07K 2317/73* (2013.01); *C07K 2317/76* (2013.01); *C07K 2317/92* (2013.01)

(56) References Cited

U.S. PATENT DOCUMENTS

| | | | |
|---|---|---|---|
| 2012/0321591 A1 | 12/2012 | Doppalapudi et al. | |
| 2014/0127209 A1 | 5/2014 | Grabstein et al. | |
| 2016/0326266 A1* | 11/2016 | Fu | C07K 16/468 |
| 2018/0194859 A1* | 7/2018 | Kaufmann | C07K 16/46 |

FOREIGN PATENT DOCUMENTS

| | | | |
|---|---|---|---|
| WO | 2011069104 A2 | 6/2011 | |
| WO | 2011090762 A1 | 7/2011 | |
| WO | 2012/120198 A1 | 9/2012 | |
| WO | 201303555 | * | 1/2013 |
| WO | 2013003555 A1 | 1/2013 | |
| WO | 2013155526 | * | 10/2013 |

OTHER PUBLICATIONS

Witte, et al.: "Preparation of unnatural N-to-N and C-to-C protein fusions", Proc Natl Acad Science; vol. 109, No. 30, pp. 11993-1998, (Jul. 2012).

Witte, et al.: "Production of unnaturally linked chimeric proteins using a combination of sortase-catalyzed transpeptidation and click chemistry", Nature Protocols, vol. 8, No. 9, pp. 1808-1819, (Aug. 2013).

Wagner, et al.: "Bispecific antibody generated with sortase and click chemistry has broad antiinfluenza virus activity", Proceedings of the National Academy of Sciences of the United States of America, vol. 111, No. 47, pp. 16820-16825, (Nov. 2014).

Supplementary European Search Report, relating to corresponding European Application No. 15792450, completed on Oct. 12, 2017 and dated Oct. 23, 2017.

Liu, et al., "Disulfide bond structures of IgG molecules Structural variations, chemical modifications and possible impacts to stability and biological function," Merck Research Laboratories, mAbs 4:1, 17-23; Jan./Feb. 2012.

* cited by examiner

Non-reduced    Reduced

Figure 8
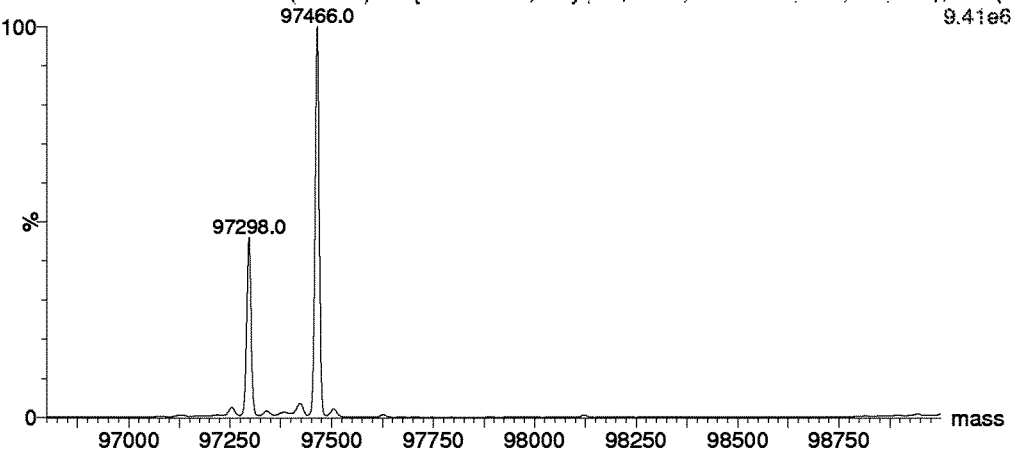
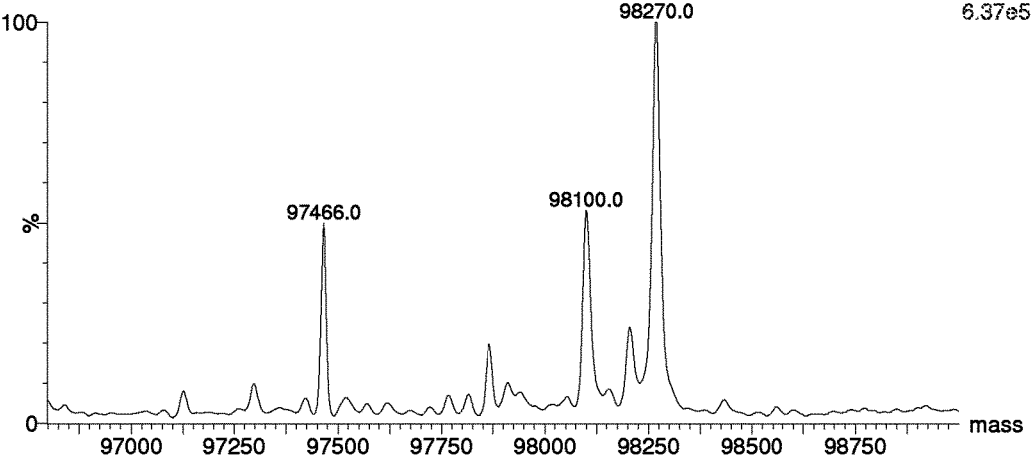
Figure 8

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Hinge region fragment

<400> SEQUENCE: 1

Cys Pro Pro Cys
1

<210> SEQ ID NO 2
<211> LENGTH: 4
```

```
<212> TYPE: PRT
<213> ORGANISM: Artificial Sequence
<220> FEATURE:
<223> OTHER INFORMATION: Hinge region fragment

<400> SEQUENCE: 2

Cys Pro Ser Cys
1

<210> SEQ ID NO 3
<211> LENGTH: 4
<212> TYPE: PRT
<213> ORGANISM: Artificial Sequence
<220> FEATURE:
<223> OTHER INFORMATION: Hinge region fragment

<400> SEQUENCE: 3

Ser Pro Pro Cys
1

<210> SEQ ID NO 4
<211> LENGTH: 4
<212> TYPE: PRT
<213> ORGANISM: Artificial Sequence
<220> FEATURE:
<223> OTHER INFORMATION: Hinge region fragment

<400> SEQUENCE: 4

Ser Pro Ser Cys
1
```

CHEMICALLY-LOCKED BISPECIFIC ANTIBODIES

CROSS REFERENCE TO RELATED APPLICATION

This application is a 35 U.S.C. § 371 national stage filing of International Application No. PCT/US2015/030054, filed May 10, 2015, which in turn claims the benefit of priority of U.S. Provisional Application No. 61/991,508 filed 10 May 2014. The entire contents of each of the foregoing applications are incorporated herein by reference.

TECHNICAL FIELD

The present disclosure provides a process for forming chemically-locked bispecific or heterodimer antibodies, preferably in the IgG class, in high specificity and with high homogeneity. More specifically, the present disclosure provides a chemically-locked bispecific IgG class antibody having a linkage region joined with bio-orthogonal click chemistry.

BACKGROUND

Human immunoglobulin G or IgG antibodies exist in four subclasses, each with distinct structural and functional properties. IgGs are composed of two heavy chain-light chain pairs (half-antibodies) which are connected via inter-heavy chain disulfide bonds directly linking Cys residues in the hinge region (EU-index numbering: cysteine residues 226 and 229; Kabat numbering: cysteine residues 239 and 242). Human IgG4 molecules exist in various molecular forms which differ by the absence or presence of inter-heavy chain disulfide bonds.

A wide variety of recombinant antibody formats have been developed, such as, tetravalent bispecific antibodies by fusion of an IgG antibody format and single chain domains (Coloman et al., Nature Biotech 15 (1997) 159-163; WO 2001/077342; and Morrison, Nature Biotech 25 (2007) 1233-1234). Another format has the antibody core structure (IgA, IgD, IgE, IgG or IgM) no longer retained, such as dia-, tria- or tetrabodies, minibodies, several single chain formats (scFv, Bis-scFv). But such formats are capable of binding two or more antigens (Holliger et al., Nature Biotech 23 (2005) 1126-1136; Fischer and Leger, Pathobiology 74 (2007) 3-14; Shen et al., J. Immunological Methods 318 (2007) 65-74; and Wu et al., Nature Biotech. 25 (2007) 1290-1297).

A method for separating or preferentially synthesizing dimers which are linked via at least one inter-chain disulfide linkage from dimers which are not linked via at least one interchain disulfide linkage from a mixture comprising the two types of polypeptide dimers is reported in US 2005/0163782.

Bispecific antibodies have difficulty producing materials in sufficient quantity and quality using traditional hybrid hybridoma and chemical conjugation methods. Further, WO2005/062916 and U.S. patent application 2010/0105874 describe how to form bispecific antibodies by reducing antibody "AA" and antibody "BB" to separate the disulfide bonds into single heavy-light chain units (A or B) with a single binding region (wherein both A and B bind to different targets). Then the antibodies allow the disulfide bonds to undergo isomerization such that antibodies AB, BA, AA and BB are reformed at a probability of about 25% each. However, both AB and BA are the same bispecific antibodies and therefore represent, at best, about a 50% yield. Therefore, this requires additional steps to separate the desired bispecific antibodies formed from the original reconstituted antibodies. However, U.S. patent application 2010/0105874 points to the hinge region in IgG4 having a sequence of CPSC and stating: "the CPSC sequence results in a more flexible core hinge and the possibility to form intra-chain disulfide bonds . . . it is believed that antibodies having an IgG4-like core hinge sequence may have an intrinsic activity for rearrangement of disulfide bonds, which is simulated by the conditions used in the methods of the invention." (paragraph 0013). In addition, other forms of bispecific antibodies have been made with a "knob and hole" structure made by altering the sequence of the heavy chains of antibodies A and B.

Therefore, the present disclosure provides a process to produce chemically-locked bispecific IgG antibodies that address the need in the art for a much higher yield of bispecific antibodies and with better stability than the knob and hole methods that alter amino acid sequences in the fixed antibody regions.

SUMMARY

The present disclosure provides a process for generation of a chemically-locked bispecific antibody "AB" or "BA" from an IgG 1, IgG2 or IgG4 class antibody or Fab2 fragment thereof "A" and an IgG1, IgG2 or IgG4 class antibody or Fab2 fragment thereof "B." The process comprises:

(a) contacting a first antibody "A" with a reducing agent under conditions sufficient to cleave substantially all disulfide linkages between the heavy chains in the hinge region to yield a pair of first antibody fragments A', each comprising a single light chain attached to a single heavy chain, the heavy chain having one or more reactive thiol groups formed from the reduction of said disulfide linkages;

(b) attaching a first hetero-bi-functional linker to the first antibody fragment A', wherein the first hetero-bi-functional linker comprises (i) a first thiol-reactive functional group for covalent attachment to a reactive thiol group of the heavy chain of the first antibody fragment A', and (ii) an azide, to form an azide functionalized first antibody fragment;

(c) contacting the second antibody "B" with a reducing agent under conditions sufficient to cleave substantially all disulfide linkages between the heavy chains in the hinge region to yield a pair of second antibody fragments B', each comprising a single light chain attached to a single heavy chain, the heavy chain having one or more reactive thiol groups formed from the reduction of said disulfide linkages;

(d) attaching a second hetero-bi-functional linker to said second antibody fragment B', said second hetero-bi-functional linker comprising: (i) a second thiol-reactive functional group for covalent attachment to a reactive thiol group of said heaving chain of said second antibody fragment; and (ii) an alkyne; to form an alkyne functionalized second antibody fragment;

(e) reacting said azide functionalized first antibody fragment with said alkyne functionalized second antibody fragment to covalently attach said first antibody fragment to said second antibody fragment via 1,3-dipolar cycloaddition of said azide to said alkyne, to form a chemically-locked bi-specific antibody "AB" or "BA."

The step of reducing the disulfide linkages in the hinge region is preferably carried out without substantially reducing the disulfide linkages between the heavy chains and light chains, by which is meant that, in some embodiments, at least about 90%, or at least about 95%, or at least about 99% of such disulfide linkages between the heavy chains and light chains remain intact following cleavage of the disulfide bonds in the hinge region.

Preferably, he first hetero-bi-functional linker has the form Q-L-N$_3$, wherein Q is a thiol-reactive functional group, L is a hydrocarbon linker, and N$_3$ is an azide. Preferably, the thiol-reactive functional group Q is an alkyl halide (e.g., an alkyl chloride, bromide, or iodide), benzyl halide, maleimide, halo-maleamide (bromomaleimide), or dihalo-maleimide (dibromomaleimide). Preferably, L is a hydrocarbon linker having from 3-60 atoms (e.g., more typically from 6-50) in the direct chain between Q and N$_3$. More preferably, L is a polyalkylene oxide (PEF) group or L is a polymer wherein each mer unit is —(CH$_2$CH$_2$—O)$_n$— or —(O—CH$_2$CH$_2$)$_n$— (wherein "n" is independently an integer from 1-20, more typically from 1-8).

Preferably, the first hetero-biofunctional linker (attached to the first antibody fragment) is:

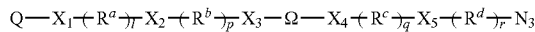

wherein Q can be any group suitable for ligating a linker onto the antibody fragment, but is preferably capable of covalently bonding with a thiol from a cysteine residue in the hinge region of the heavy chain. Exemplary groups Q are:

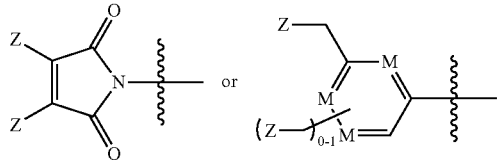

wherein Z is independently selected from the group consisting of H, Br, I, and SPh. Preferably, at least one occurrence of Z is not H, although in the case of the maleimide Z may be hydrogen at each occurrence. M is independently CR* or N.

$X_1$, $X_2$, $X_3$, $X_2$, $X_4$ and $X_5$ are independently selected from the group consisting of a bond (i.e., it is absent), —O—, —NR$^N$—, —N=C—, —C=N—, —N=N—, —CR*=CR*— (cis or trans), —C≡C—, —(C=O)—, —(C=O)—O—, —(C=O)—NR$^N$—, —(C=O)—(CH$_2$)$_n$—, —(C=O)—O—(CH$_2$)$_n$—, —(C=O)—NR$^N$—(CH$_2$)$_n$—, and —(C=O)—NR$^N$—(CH$_2$CH$_2$—O)$_n$—, wherein "n" is either zero or an integer from 1-10;

$R^a$, $R^b$, $R^c$, and $R^d$ are independently selected from the group consisting of —O—, —NR$^N$—, —CH$_2$—, —(CH$_2$)$_n$—, —(CR*$_2$)$_n$—, —(CH$_2$CH$_2$—O)$_n$—, —(CR*$_2$CR*$_2$—O)$_n$—, —(O—CH$_2$CH$_2$)$_n$—, —(O—CR*$_2$CR*$_2$)$_n$—, —CR*=CR*-(cis or trans), —N=C—, —C=N—, —N=N—, —C≡C—, —(C=O)—, —(CH$_2$)$_n$—(C=O)—, —(C=O)—(CH$_2$)$_n$—, —(CH$_2$)$_n$(C=O)—(CH$_2$)$_n$—, —O—(C=O)—, —(C=O)—O—, —O—(C=O)—O—, —(CH$_2$)$_n$—(C=O)—O—, —O—(C=O)—(CH$_2$)$_n$—, —(C=O)—O—(CH$_2$)$_n$—, —(CH$_2$)$_n$—O—(C=O)—, —(CH$_2$)$_n$—(C=O)—O—(CH$_2$)$_n$—, —(CH$_2$)$_n$—O—(C=O)—(CH$_2$)$_n$—, —NR$^N$—(C=O)—, —(C=O)—NR$^N$—, —NR$^N$—(C=O)—O—, —O—(C=O)—NR$^N$—, —NR$^N$—(C=O)—NR$^N$—, —(CH$_2$)$_n$—(C=O)—NR$^N$—, —(C=O)—NR$^N$—, —NR$^N$—(C=O)—(CH$_2$)$_n$, —(C=O)— NR$^N$—(CH$_2$)$_n$—, —(CH$_2$)$_n$—NR$^N$—(C=O)—, —(CH$_2$)$_n$—(C=O)—NR$^N$—(CH$_2$)$_n$—, —(CH$_2$)$_n$—NR$^N$—(C=O)—(CH$_2$)$_n$—, —(C=O)—NR$^N$—(CH$_2$CH$_2$—O)$_n$—, —(CH$_2$CH$_2$—O)$_n$—(C=O)—NR$^N$—, —(CH$_2$)$_n$—(C=O)—NR$^N$—(CH$_2$CH$_2$—O)$_n$—, —(CH$_2$CH$_2$—O)$_n$—(C=O)—NR$^N$—(CH$_2$)$_n$—, and a 2-8 membered cyclic hydrocarbon, heterocycle, aryl, or heteroaryl ring; wherein "n" is independently a zero or an integer from 1-10; and wherein "l", "p", "q", and "r" are independently zero or an integer from 1-10;

Ω is either a bond (i.e., it is absent) or is a C$_{3-26}$ hydrocarbon ring or fused ring system, optionally comprising up to four fused rings, each ring having from 3-8 members and optionally comprising from 1-4 heteroatoms selected from O, S, and N in each ring. Preferably, Ω is a 1,2,3-triazole ring fused to a cyclooctane ring or fused to an 8-membered heterocyclic ring or ring system.

R* and R$^N$ are, independently at each occurrence, either H or a C$_{1-12}$ hydrocarbon, optionally substituted with 1-6 heteroatoms selected from halogen, O, S, and N; and wherein any two groups R* and/or R$^N$ may together from a 3-8 membered ring.

The second hetero-bi-functional linker has the form Q-L-G, wherein Q is a thiol-reactive functional group, L is a hydrocarbon linker, and G is an alkyne-containing group. The thiol-reactive functional group Q is selected from the group consisting of an alkyl halide (e.g., an alkyl chloride, bromide, or iodide), benzyl halide, maleimide, halo-maleamide (such as bromomaleimide), and dihalo-maleimide (such as dibromomaleimide). L is a hydrocarbon linker having from 3-60 atoms (e.g., preferably from 6-50) in a direct chain between Q and G. Preferably, L is a polyalkylene oxide group (PEG), Preferably, L is a polymer of units —(CH$_2$CH$_2$—O)$_n$— or —(O—CH$_2$CH$_2$)$_n$— (wherein "n" is independently an integer from 1-20, more typically from 1-8).

G is any alkyne containing group that is capable of undergoing cycloaddition with an azide. In some embodiments, G comprises a terminal alkyne, such as —C≡CH. In other embodiments, G comprises ring or ring system having a —C≡C— bond in the ring. In one embodiment, G comprises a C8 ring having a —C≡C— bond. In one embodiment, the —C≡C— containing ring is strained.

The second hetero-biofunctional linker has the form:

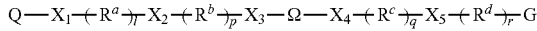

Q is the same or different that in the first hetero-bifunctional linker. Q is typically a thiol-reactive group of the form:

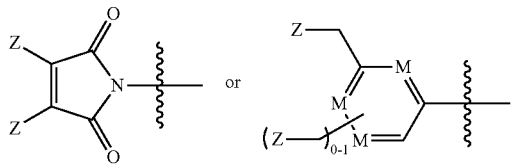

wherein Z is independently selected at each occurrence from H, Br, I, and SPh. In some embodiments, at least one occurrence of Z is not H, although in the case of the maleimide Z may be hydrogen at each occurrence. M is independently at each occurrence either CR* or N.

G is typically a $C_{8-20}$ hydrocarbon group comprising a —C≡C— bond capable of undergoing a 1,3 dipolar cycloaddition reaction with an azide. In some embodiments, G has the form —C≡C—H. In other embodiments, G comprises a ring having a —C≡C— bond. In particular, G may comprise an 8-membered ring having a triple bond (e.g., a cyclooctyne). The ring may optionally be fused to one, two, or more additional rings, which will typically be $C_{3-6}$ cyclic hydrocarbon rings, including aryl, heteroaryl, and heterocycles. The 8-membered ring containing the triple bond may include one or more (e.g., 1-4) heteroatoms, such as nitrogen and oxygen, in the ring. In one embodiment, the 8-membered ring contains a nitrogen atom in the ring which provides a point of attachment to L as in the exemplary structure shown below:

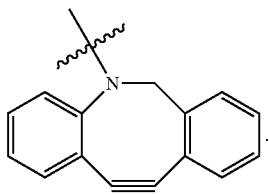 [SMILES: *N1Cc2ccccc2C#Cc2ccccc21]

Preferably, G has the form:

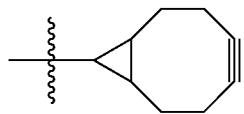

$X_1$, $X_2$, $X_3$, $X_2$, $X_4$ and $X_5$ are independently selected, at each occurrence, from the group consisting of a bond (i.e., it is absent), —O—, —NR$^N$—, —N=C—, —C=N—, —N=N—, —CR*=CR*— (cis or trans), —C≡C—, —(C=O)—, —(C=O)—O—, —(C=O)—NR$^N$—, —NR$^N$—(C=O)—, —NR$^N$—(C=O)—O—, —(C=O)—(CH$_2$)$_n$—, —(C=O)—O—(CH$_2$)$_n$—, —(C=O)—NR$^N$—(CH$_2$)$_n$—, and —(C=O)—NR$^N$—(CH$_2$CH$_2$—O)$_n$—, where "n" is either zero or an integer from 1-10;

R$^a$, R$^b$, R$^c$, and R$^d$ are independently selected, at each occurrence, from —O—, —NR$^N$—, —CH$_2$—, —(CH$_2$)$_n$—, —(CR*$_2$)$_n$—, —(CH$_2$CH$_2$—O)$_n$—, —(CR*$_2$CR*$_2$—O)$_n$—, —(O—CH$_2$CH$_2$)$_n$—, —(O—CR*$_2$CR*$_2$)$_n$—, —CR*=CR*— (cis or trans), —N=C—, —C=N—, —N=N—, —C≡C—, —(C=O)—, —(CH$_2$)$_n$—(C=O)—, —(C=O)—(CH$_2$)$_n$—, —(CH$_2$)$_n$—(C=O)—(CH$_2$)$_n$—, —O—(C=O)—, —(C=O)—O—, —O—(C=O)—O—, —(CH$_2$)$_n$—(C=O)—O—, —O—(C=O)—(CH$_2$)$_n$, —(C=O)—O—(CH$_2$)$_n$—, —(CH$_2$)$_n$—O—(C=O)—, —(CH$_2$)$_n$—(C=O)—O—(CH$_2$)$_n$—, —(CH$_2$)$_n$—O—(C=O)—(CH$_2$)$_n$—, —(CH$_2$)$_n$—O—, —(C=O)—(CH$_2$)$_n$—, —NR$^N$—(C=O)—, —(C=O)—, —NR$^N$—(C=O)—O—, —O—(C=O)—NR$^N$—, —NR$^N$—(C=O)—NR$^N$—, —(CH$_2$)$_n$—(C=O)—NR$^N$—, —NR$^N$—(C=O)—(CH$_2$)$_n$—, —(C=O)—NR$^N$—(CH$_2$)$_n$—, —(CH$_2$)$_n$—NR$^N$—(C=O)—, —(CH$_2$)$_n$—(C=O)—NR$^N$—(CH$_2$)$_n$—, —(CH$_2$)$_n$—NR$^N$—(C=O)—(CH$_2$)$_n$—, —(C=O)—NR$^N$—(CH$_2$CH$_2$—O)$_n$—, —(CH$_2$CH$_2$—O)$_n$—(C=O)—NR$^N$—, —(CH$_2$)$_n$—(C=O)—NR$^N$—(CH$_2$CH$_2$—O)$_n$—, —(CH$_2$CH$_2$—O)$_n$—(C=O)—NR$^N$—(CH$_2$)$_n$— or a 2-8 membered cyclic hydrocarbon, heterocycle, aryl, or heteroaryl ring; where "n" is, independently at each occurrence, either zero or an integer from 1-10; and where "l", "p", "q", and "r" are, independently, either zero or integers from 1-10;

Ω is either a bond (i.e., it is absent) or is a $C_{3-26}$ hydrocarbon ring or fused ring system, optionally comprising up to four fused rings, each ring having from 3-8 members and optionally comprising from 1-4 heteroatoms selected from O, S, and N in each ring. In one embodiment, Ω will comprise a 1,2,3-triazole ring fused to a cyclooctane ring or fused to an 8-membered heterocyclic ring or ring system.

R* and R$^N$ are, independently at each occurrence, either H or a $C_{1-12}$ hydrocarbon, optionally substituted with 1-6 heteroatoms selected from halogen, O, S, and N; and wherein an two groups R* and/or R$^N$ may together from a 3-8 membered ring.

The cycloaddition reaction between the azide and the alkyne may proceed through a 1,3 dipolar cycloaddition reaction. The reaction may be catalyzed by copper ions. In some embodiments, the cycloaddition reaction occurs at neutral or physiological pH.

The present disclosure further provides a method for reducing an antibody "A" with the hinge residue sequence (EU-index numbering: residues 226-229; Kabat numbering: residues 239-242) CPPC (SEQ ID NO.: 1) or CPSC (SEQ ID NO.: 2) or SPPC (SEQ ID NO.: 3) or SPSC (SEQ ID NO.: 4) and a second antibody "B" with the hinge residue sequence (residues 226-229) CPPC (SEQ ID NO.: 1) or CPSC (SEQ ID NO.: 2) or SPPC (SEQ ID NO.: 3) or SPSC (SEQ ID NO.: 4) to form half-antibody A and half-antibody-B, comprising:

(a) reducing each antibody A and antibody B, whereby the reducing conditions break any inter-chain or intra-chain disulfide bonds in a hinge region of each antibody with a hinge residue sequence (EU-index numbering: residues 226-229; Kabat numbering: residues 239-242) CPPC (SEQ ID NO.: 1) or CPSC (SEQ ID NO.: 2) or SPPC (SEQ ID NO.: 3) or SPSC (SEQ ID NO.: 4);

(b) linking a compound selected from the group consisting of:

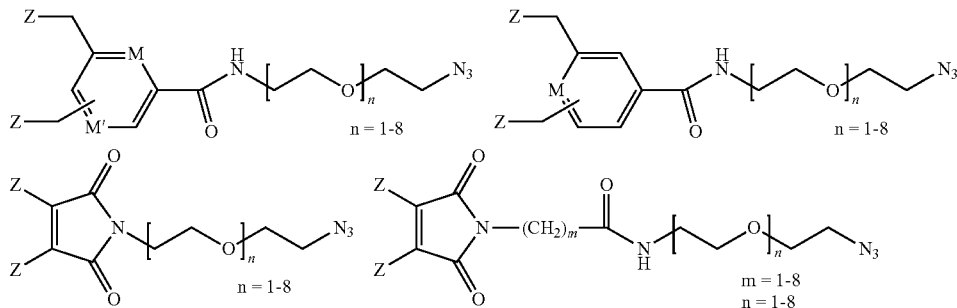

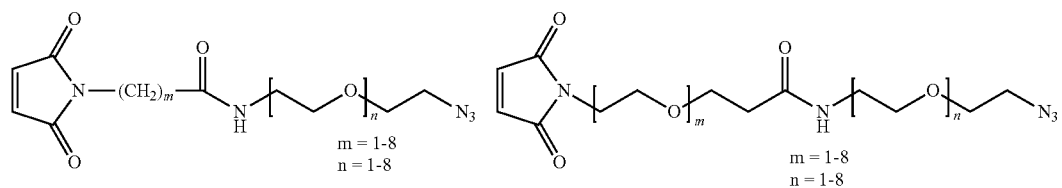
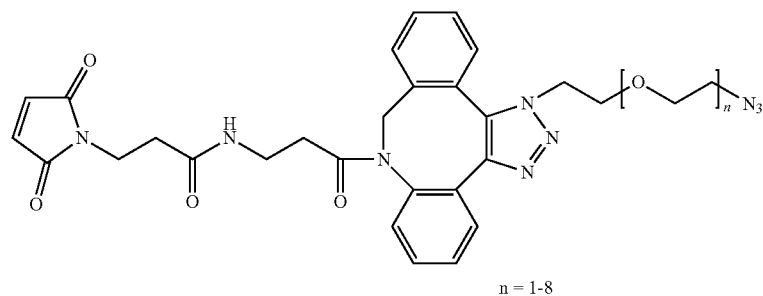
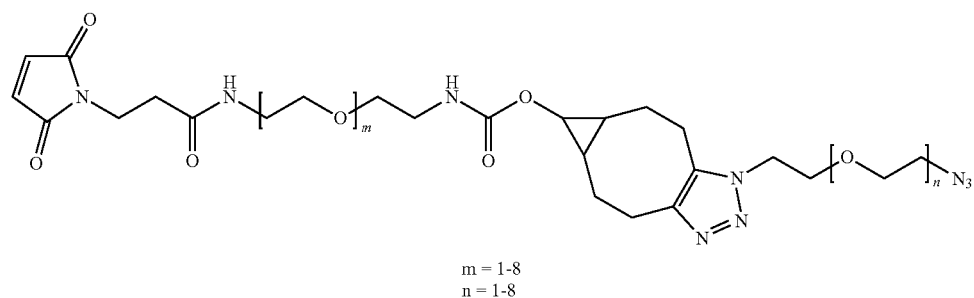
M = N, C
M' = N, C
Z = I, Br, SPh
wherein $N_3$ is —N=N=N; to one or both Cys residues (EU-index numbering: residues 226 and 229; Kabat numbering: residues 239 and 242) of the hinge core sequence of half-antibody A to form a linked half-antibody A;
(c) linking a compound selected from the group consisting of:
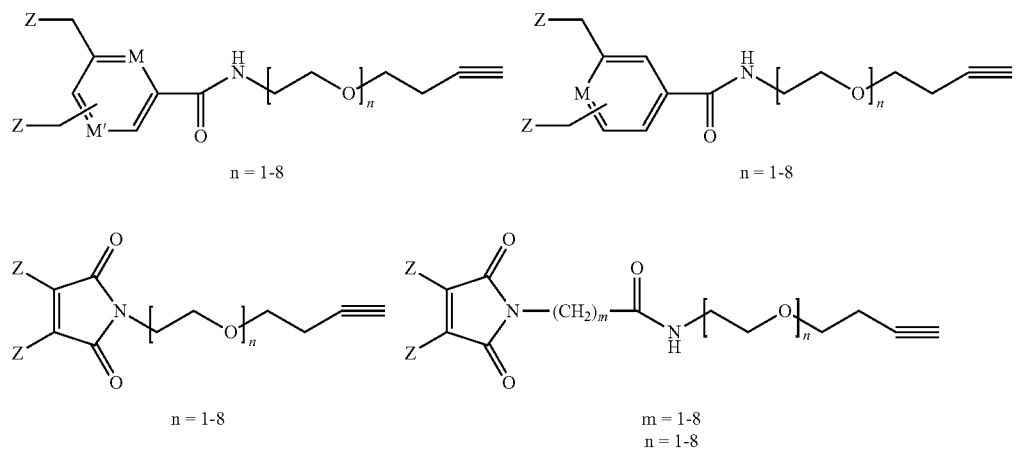

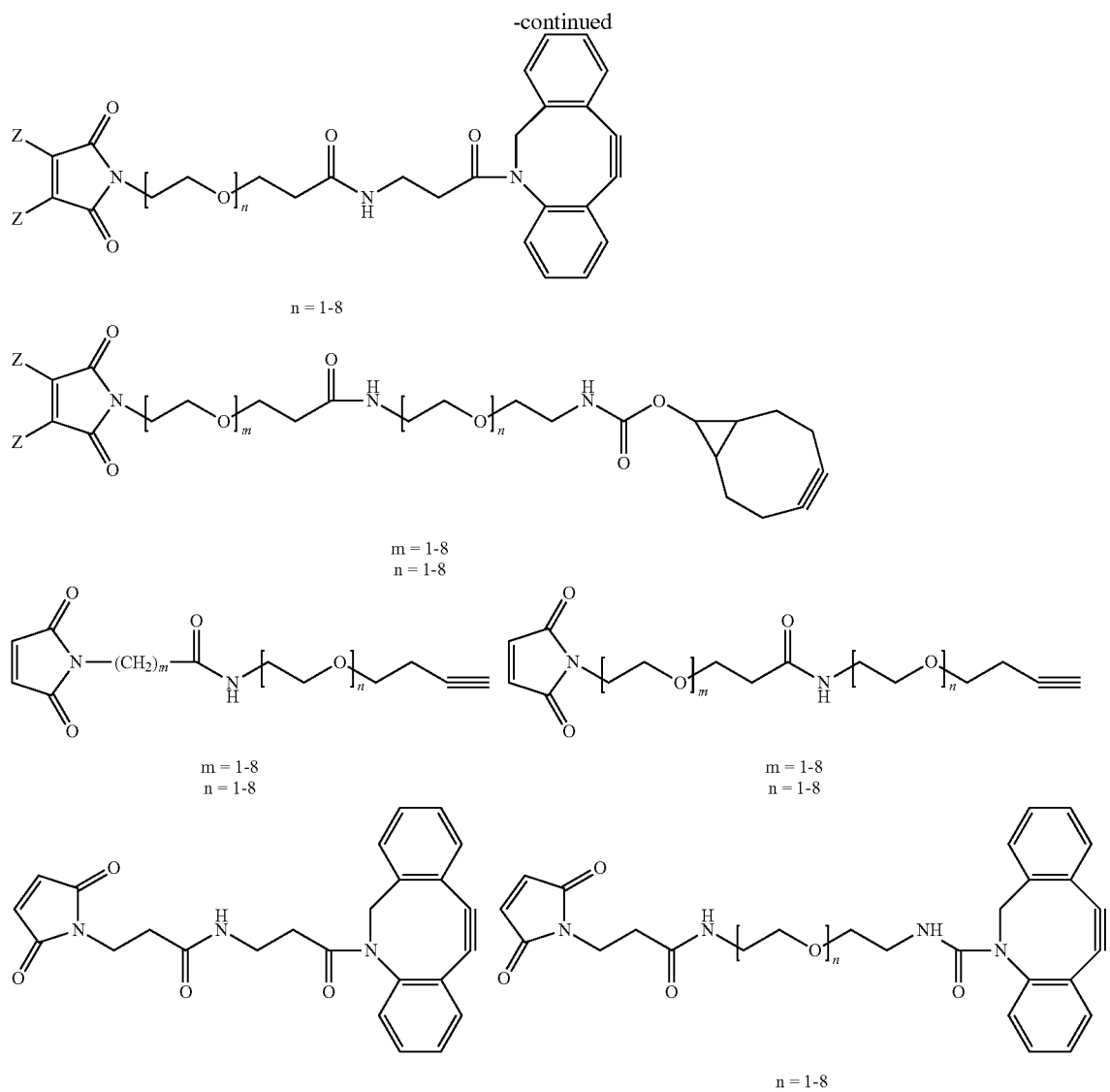

M = N, C
M' = N, C
Z = I, Br, SPh to one or both Cys residues 226 and 229 (EU-index numbering: residues 226 and 229; Kabat numbering: residues 239 and 242) of the hinge core sequence of antibody B to form a linked antibody B; and (d) incubating approximately equal molar amounts of linked antibody A with linked antibody B under neutral conditions to form the bispecific antibody AB that are linked.

Preferably, the reduction of antibody A to form half-antibody A and antibody B to form half-antibody B is conducted in a reducing agent, wherein the reducing agent is selected from the group consisting of L-cysteine, dithiothreitol, beta-mercapto ethanol, cysteamine, TCEP (tris(2-carboxyethyl)phosphine), 2-MEA (2-Mercaptoethylamine), and combinations thereof. Preferably the hinge region of antibody A, having one or two Cys residues, is linked with a moiety A having the structure selected from the group consisting of:

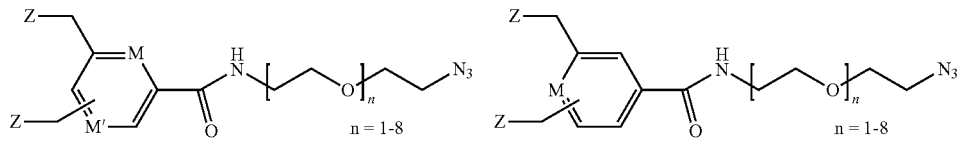

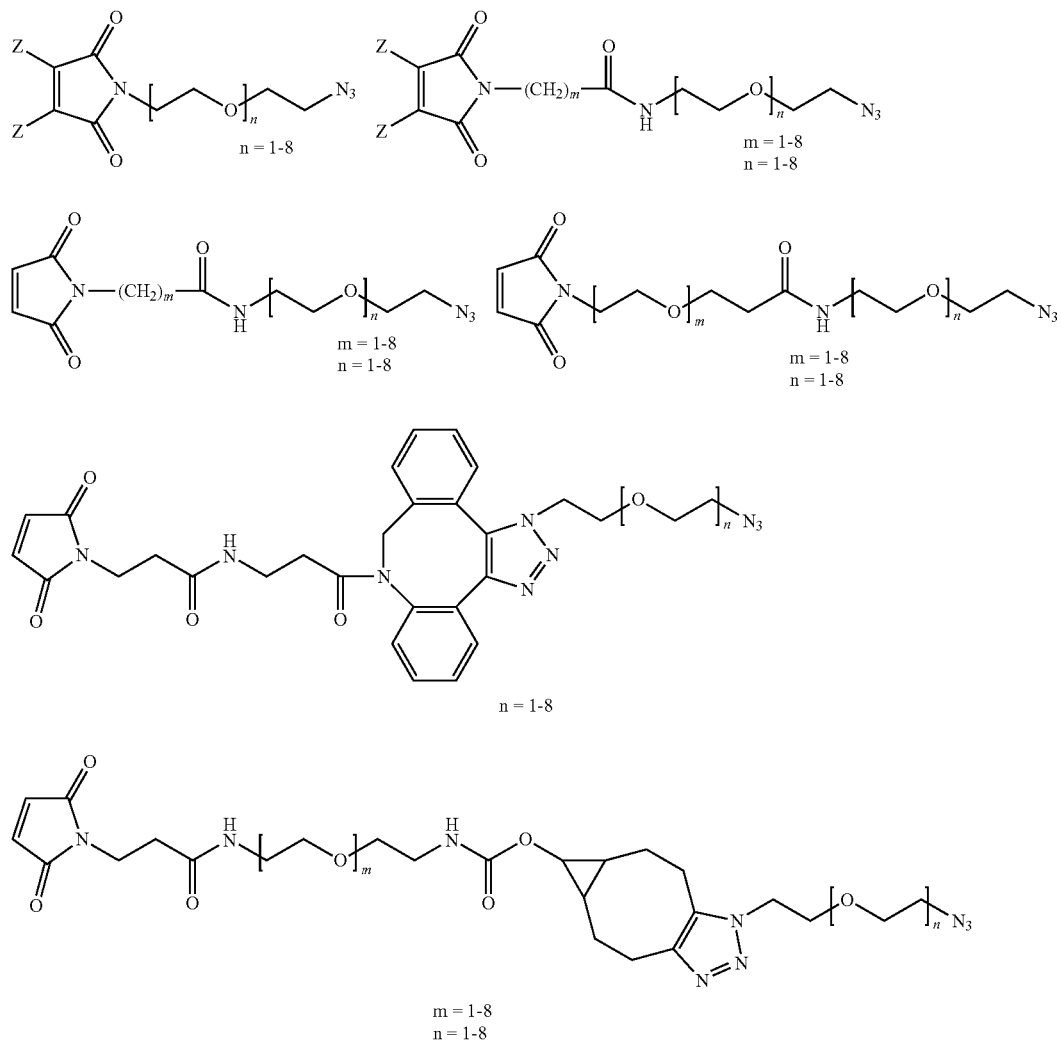
M = N, C
M' = N, C
Z = I, Br, SPh
wherein N₃ is —N═N═N. Preferably the hinge region of antibody B, having one or two Cys residues, is linked with a moiety B having the structure selected from the group consisting of:
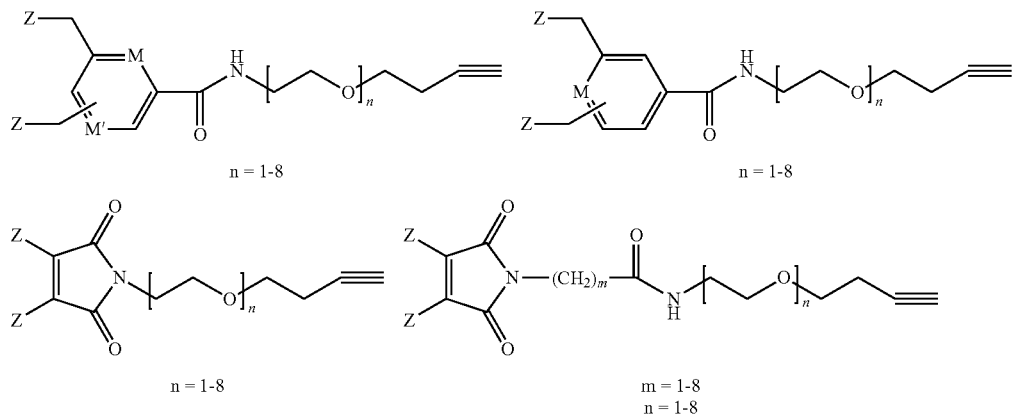

-continued

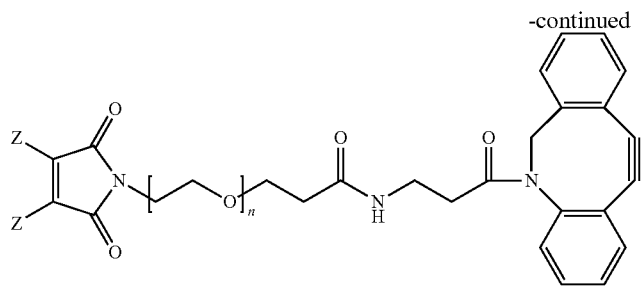

n = 1-8

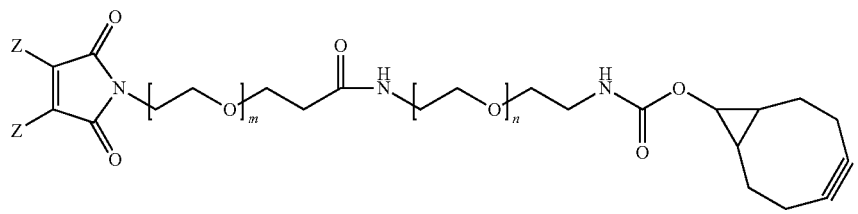

m = 1-8
n = 1-8

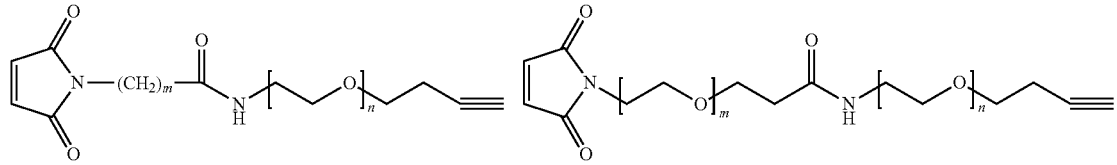

m = 1-8
n = 1-8 m = 1-8
n = 1-8

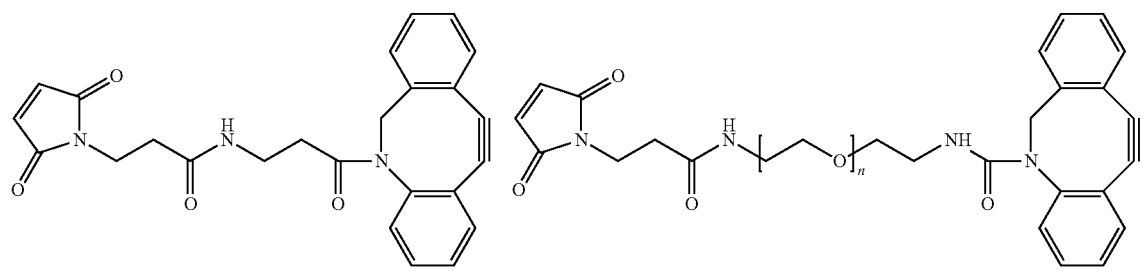

n = 1-8

M = N, C
M' = N, C
Z = I, Br, SPh to form a linked half-antibody B.

The present disclosure further provides a chemically-locked bispecific antibody AB, wherein a linked half-antibody A

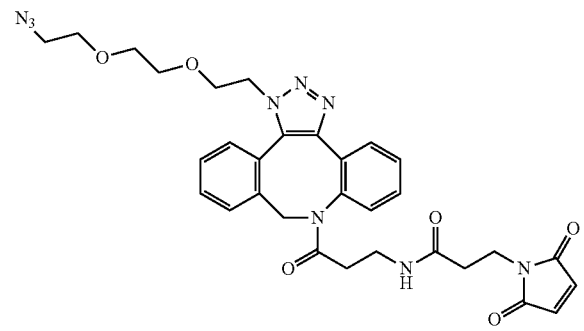

wherein N₃ is —N=N=N;

joins a linked antibody B

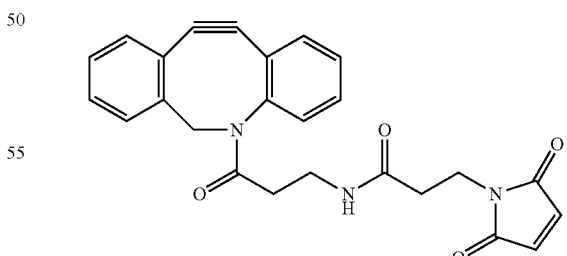

to form a bispecific antibody AB having the structure shown in FIG. 10.

The present disclosure provides a chemically-locked bispecific antibody "AB" or "BA" from an IgG class antibody "A" or fragment thereof and an IgG class antibody "B" comprising a half-antibody A having a structure selected from the group consisting of:

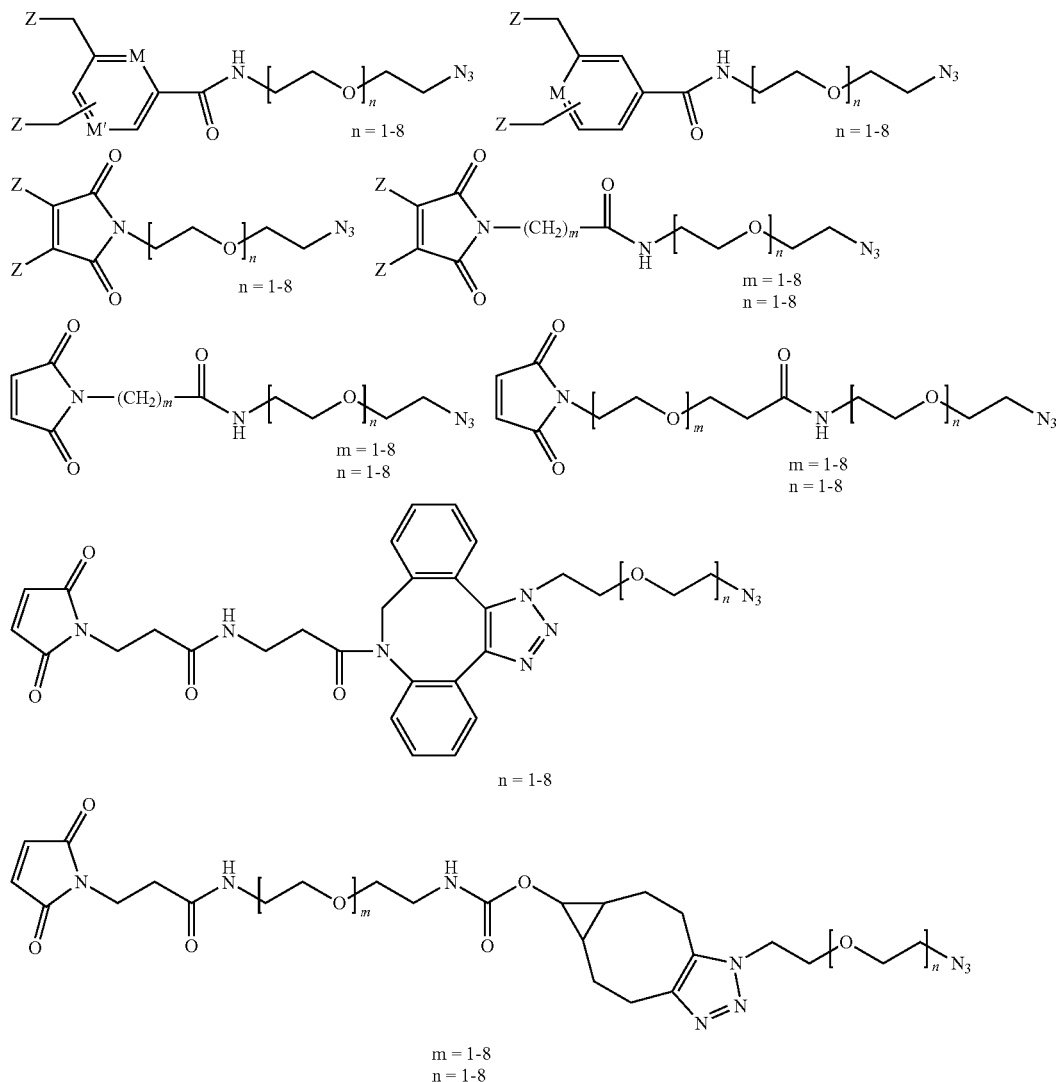
M = N, C
M' = N, C
Z = I, Br, SPh
wherein $N_3$ is —N=N=N, and wherein Z is the leaving group;
and a half-antibody B having the structure selected from the group consisting of:
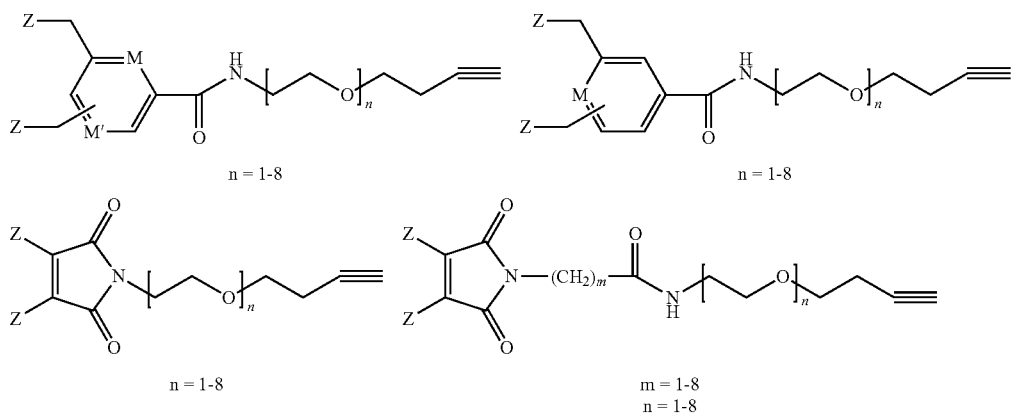

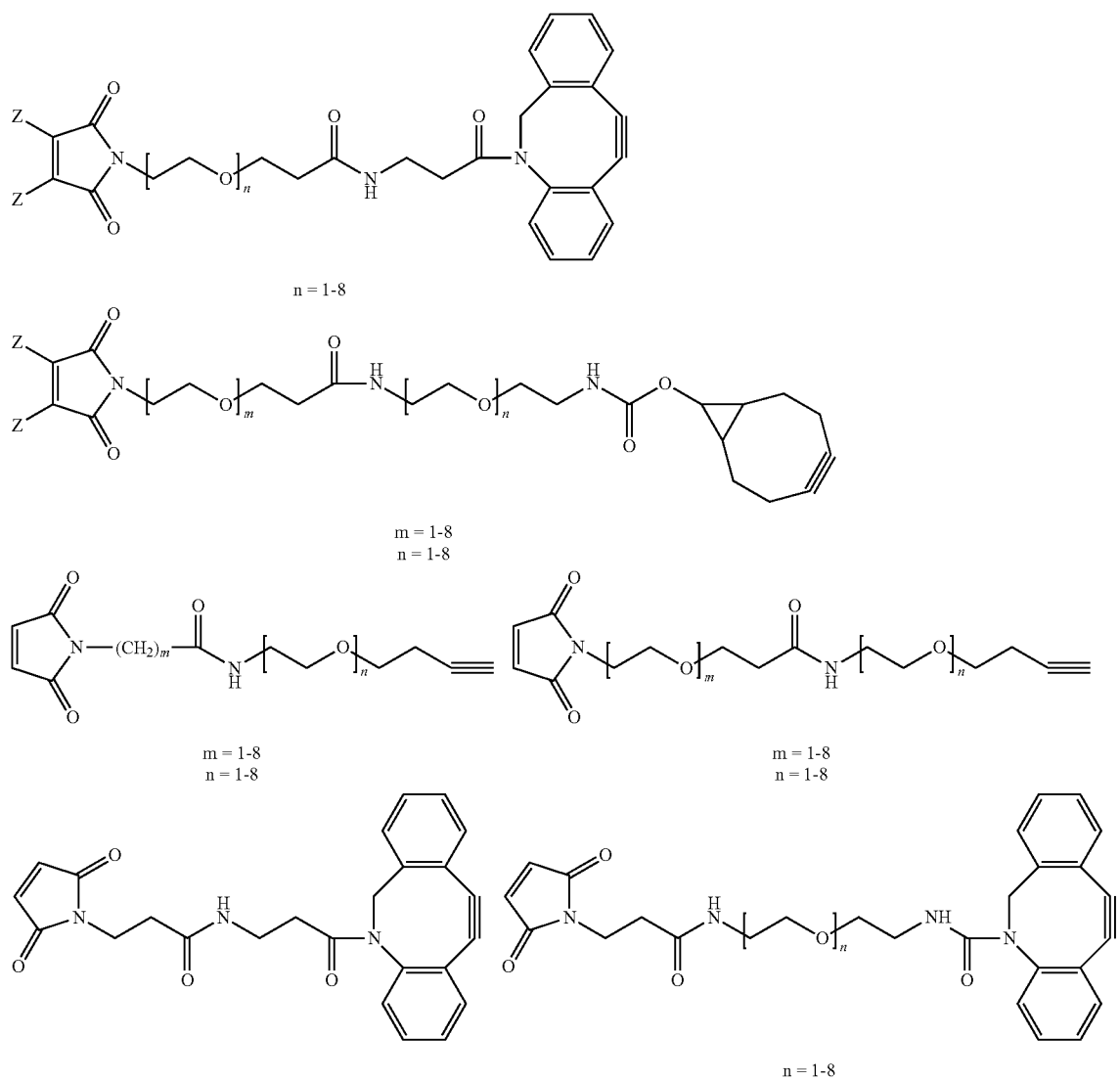

M = N, C
M' = N, C
Z = I, Br, SPh

The present disclosure further provides a bispecific antibody comprising:

(a) a first antibody fragment A', comprising a single heavy chain and light chain from an antibody A, the heavy chain having one or more reactive thiol groups;

(b) a second antibody fragment B', comprising single heavy chain and light chain, the heavy chain having one or more reactive thiol groups;

wherein, said first and second antibody fragments are covalently linked through a 1,2,3-triazole formed by a cycloaddition reaction of an azide, attached through a linker to a reactive thiol on said first antibody fragment, and an alkyne, attached through a linker to a reactive thiol on said second antibody fragment. The linkers are described above. Antibody fragments A' and B' are derived from IgG1, IgG2 or IgG4 immunoglobulins of Fab2 fragments thereof.

The present disclosure further provides an antibody fragment covalently bonded to a linker, wherein the linker comprises a $C_8$ ring having a —C≡C— bond capable of undergoing a cycloaddition reaction with an azide. The present disclosure further provides an antibody fragment covalently bonded to a linker, wherein the linker comprises an azide capable of undergoing a cycloaddition reaction with —C≡C— bond.

Preferably, the reduction of antibody A to form half-antibody A and antibody B to form half-antibody B is conducted in a reducing agent, wherein the reducing agent is selected from the group consisting of L-cysteine, dithiothreitol, beta-mercapto ethanol, cysteamine, TCEP (tris(2-carboxyethyl)phosphine), 2-MEA (2-Mercaptoethylamine), and combinations thereof. Preferably the hinge region of antibody A, having one or two Cys residues, is linked with a moiety A having the structure selected from the group consisting of:

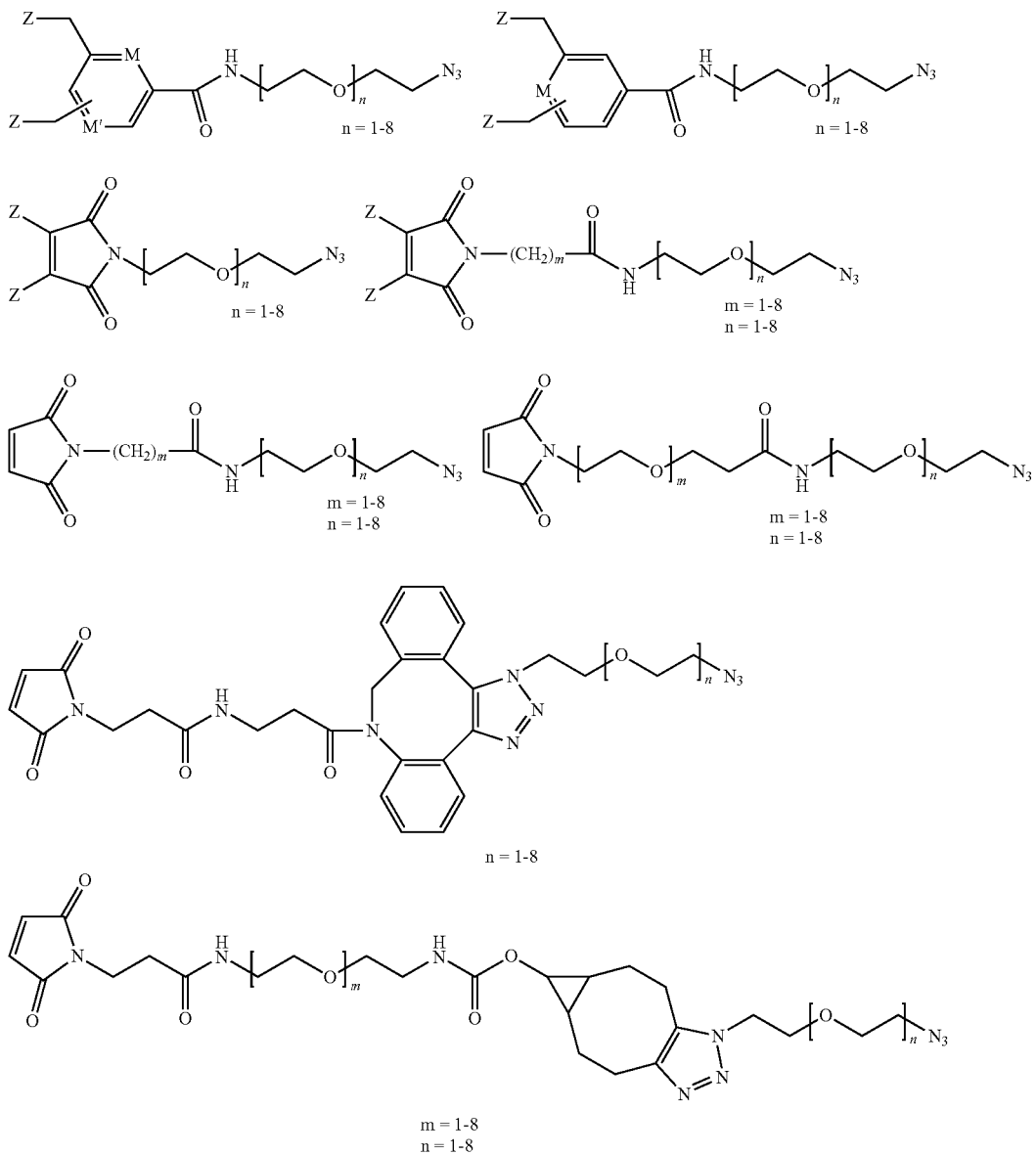
M = N, C
M' = N, C
Z = I, Br, SPh
wherein $N_3$ is —N=N=N;
to one or both Cys residues (EU-index numbering: residues 226 and 229; Kabat numbering: residues 239 and 242) of the hinge core sequence of half-antibody A to form a linked half-antibody A;
(c) linking a compound selected from the group consisting of:
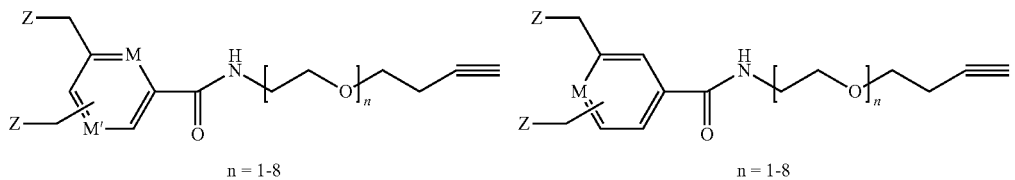

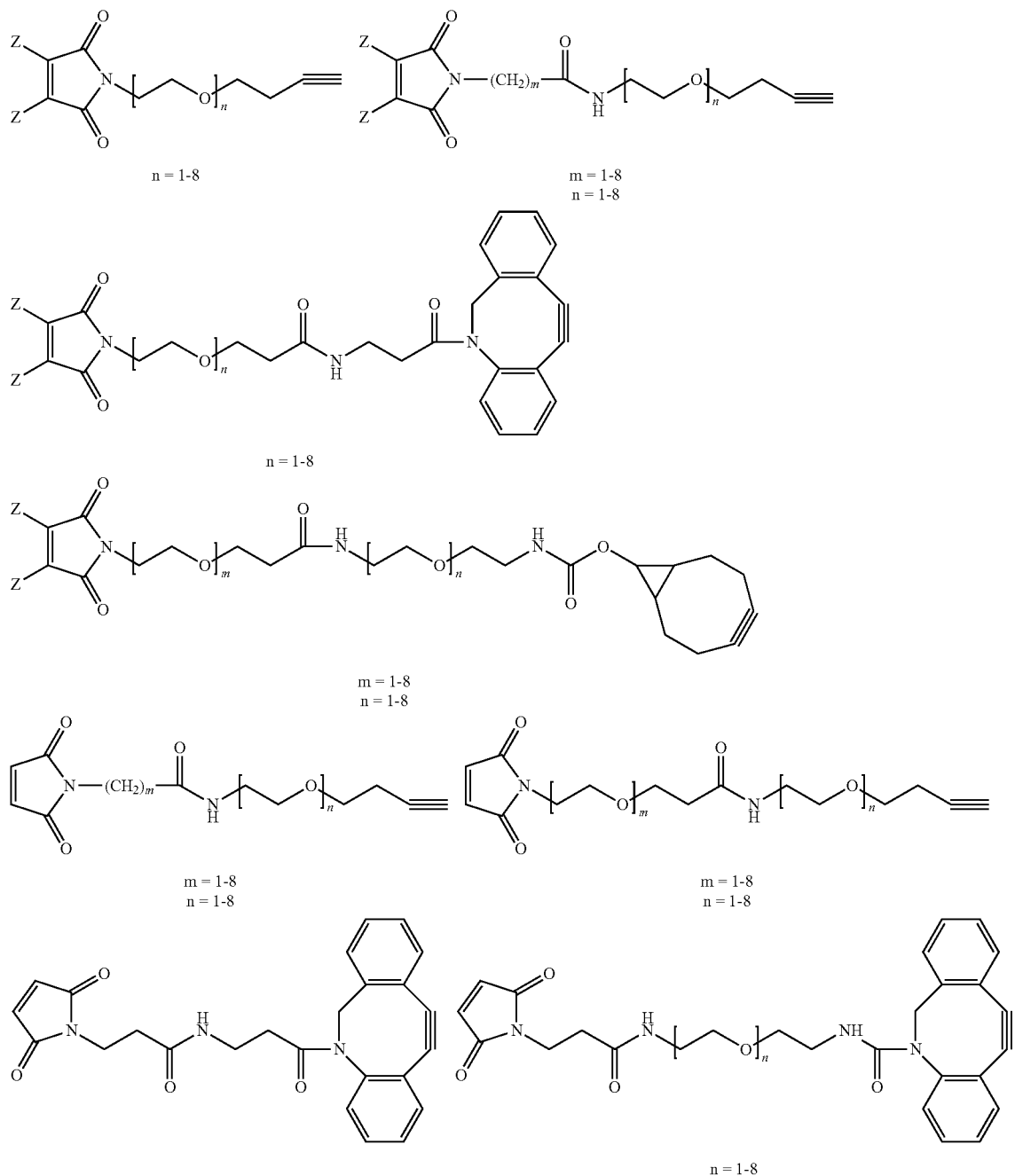

M = N, C
M' = N, C
Z = I, Br, SPh to one or both Cys residues 226 and 229 (EU-index numbering: residues 226 and 229; Kabat numbering: residues 239 and 242) of the hinge core sequence of antibody B to form a linked antibody B; and (d) incubating approximately equal molar amounts of linked antibody A with linked antibody B under neutral conditions to form the bispecific antibody AB that are linked.

Preferably, the reduction of antibody A to form half-antibody A and antibody B to form half-antibody B is conducted in a reducing agent, wherein the reducing agent is selected from the group consisting of L-cysteine, dithiothreitol, beta-mercapto ethanol, cysteamine, TCEP (tris(2-carboxyethyl)phosphine), 2-MEA (2-Mercaptoethylamine), and combinations thereof. Preferably the hinge region of antibody A, having one or two Cys residues, is linked with a moiety A having the structure selected from the group consisting of:

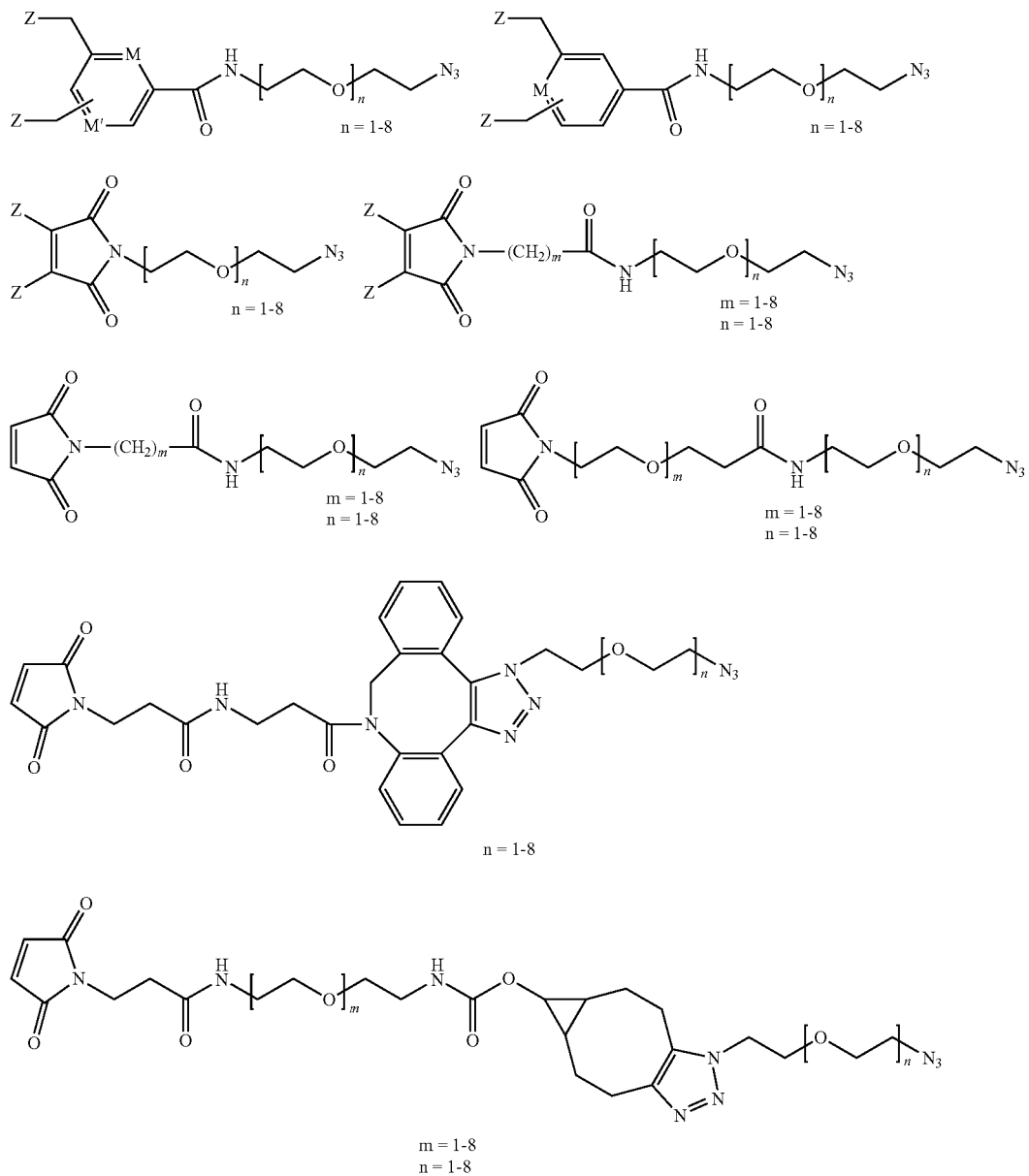
M = N, C
M' = N, C
Z = I, Br, SPh
wherein $N_3$ is —N=N=N. Preferably the hinge region of antibody B, having one or two Cys residues, is linked with a moiety B having the structure selected from the group consisting of:
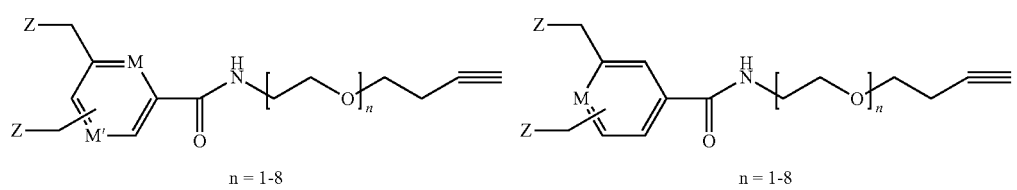

-continued
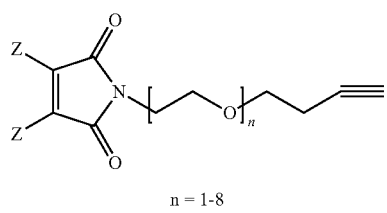
n = 1-8
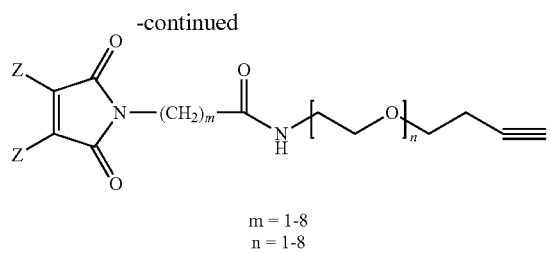
m = 1-8
n = 1-8
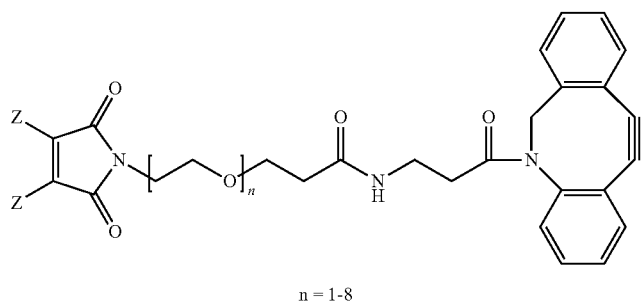
n = 1-8
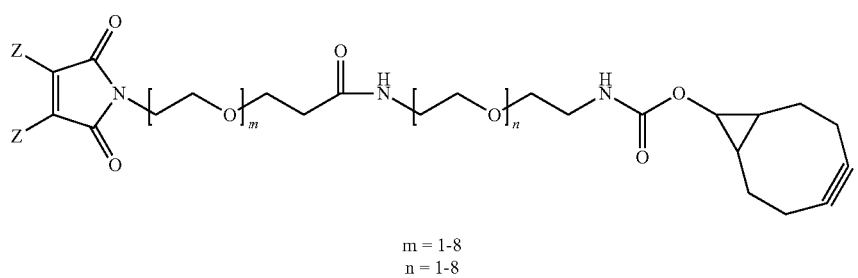
m = 1-8
n = 1-8
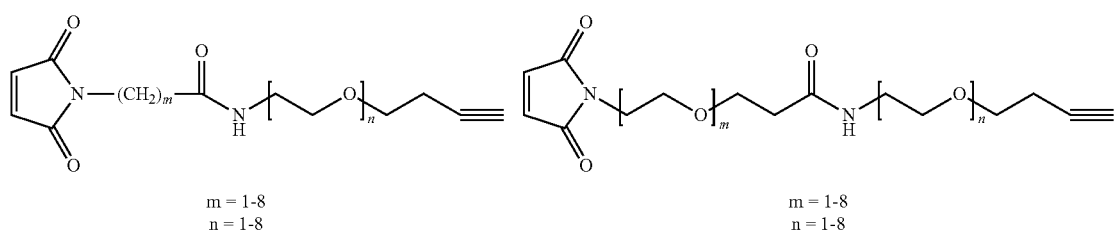
m = 1-8
n = 1-8
m = 1-8
n = 1-8
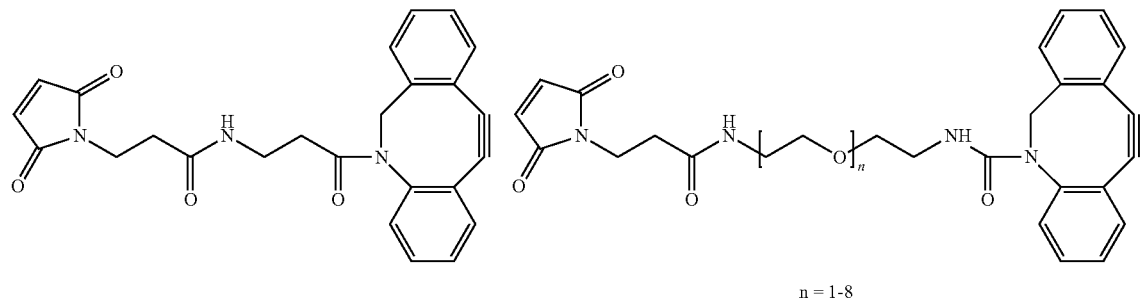
n = 1-8
M = N, C
M' = N, C
Z = I, Br, SPh
to form a linked half-antibody B.

The present disclosure further provides a chemically-locked bispecific antibody AB, wherein a linked half-antibody A

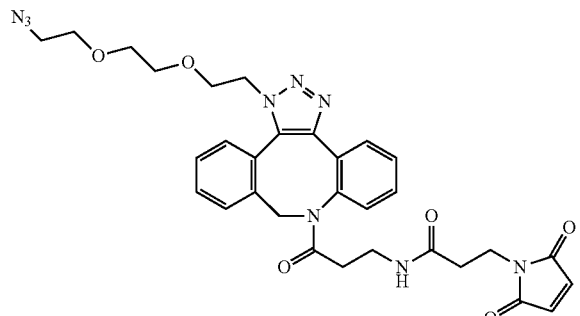

wherein $N_3$ is —N=N=N;

joins a linked antibody B

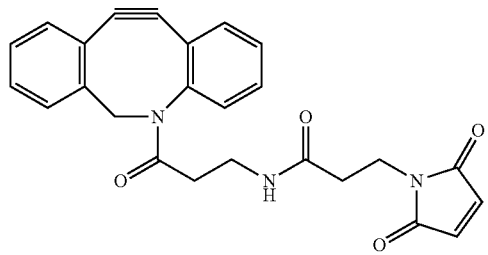 [SMILES: O=C(CCN1C(=O)C=CC1=O)NCCC(=O)N1Cc2ccccc2C#Cc2ccccc21]

to form a bispecific antibody AB having the structure shown in FIG. 10.

The present disclosure provides a chemically-locked bispecific antibody "AB" or "BA" from IgG class antibody "A" and IgG class antibody "B" comprising a half-antibody A having a structure selected from the group consisting of:

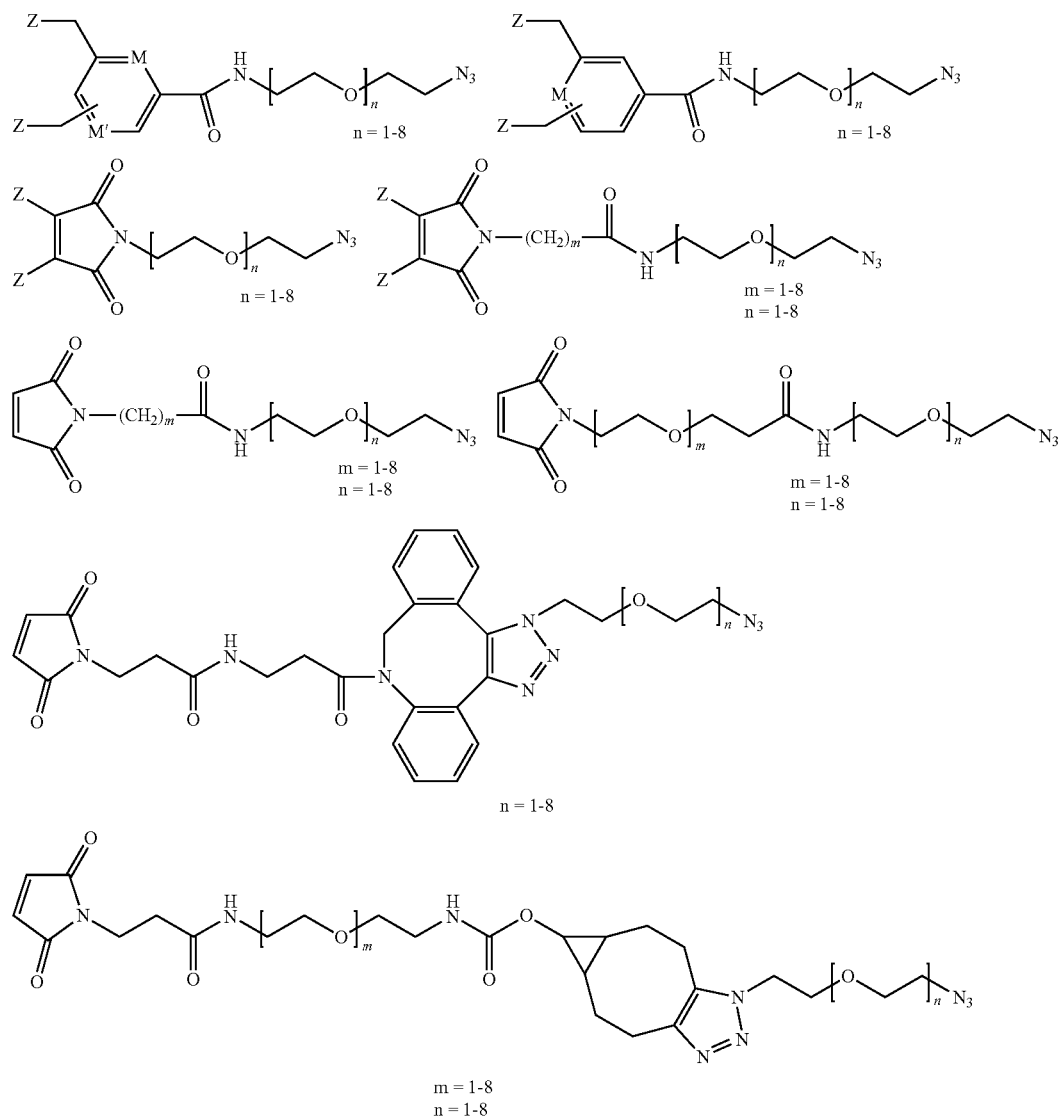

M = N, C
M' = N, C
Z = I, Br, SPh wherein $N_3$ is —N≡N≡N, and wherein Z is the leaving group that binds to;
and a half-antibody B having the structure selected from the group consisting of:
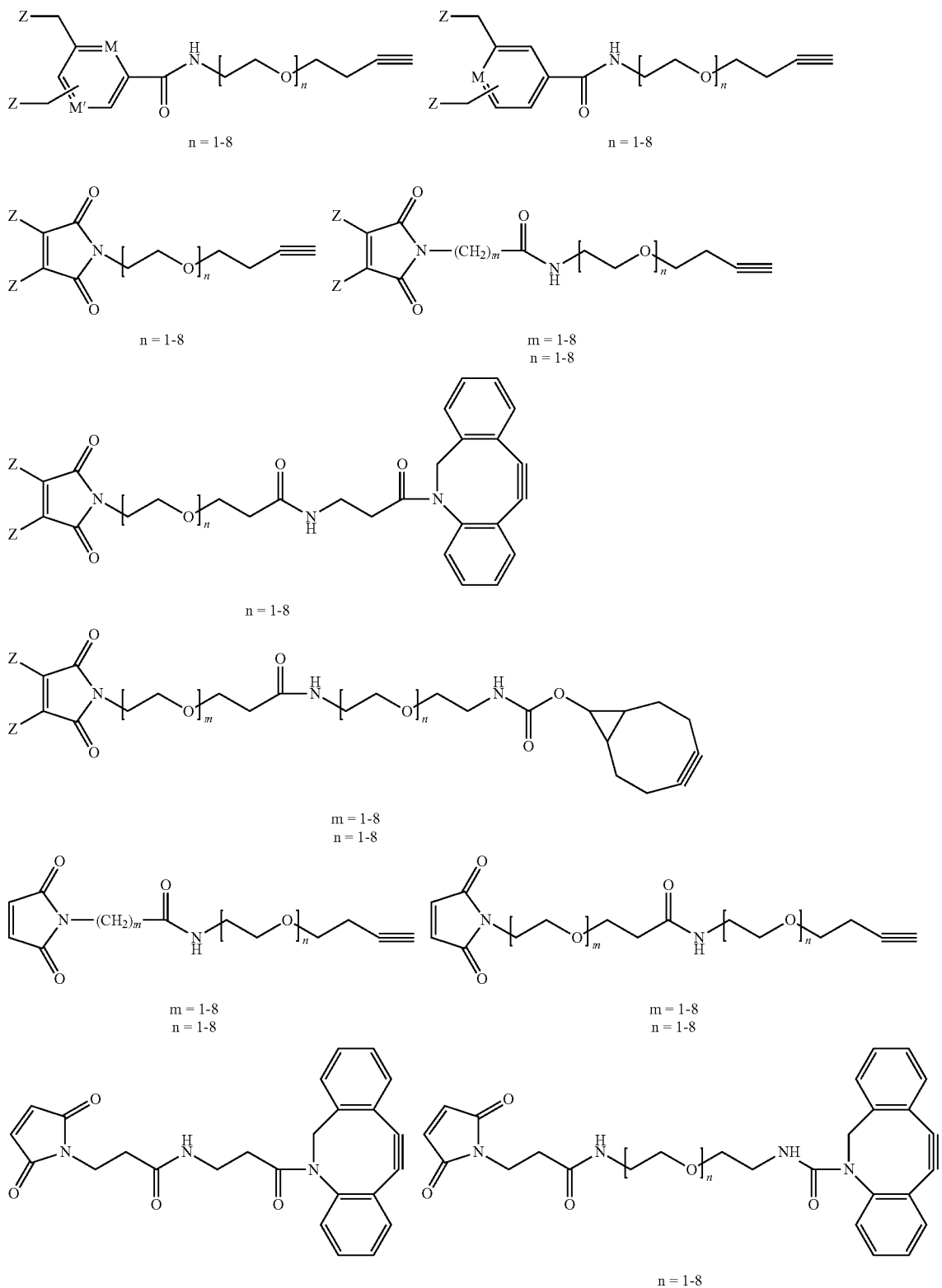
M = N, C
M' = N, C
Z = I, Br, SPh

BRIEF DESCRIPTION OF THE DRAWINGS

FIG. 8 shows MS analysis of (Fab)$_2$ from starting mAb (top) and cross-link products (bottom).

DETAILED DESCRIPTION

Figure 1:
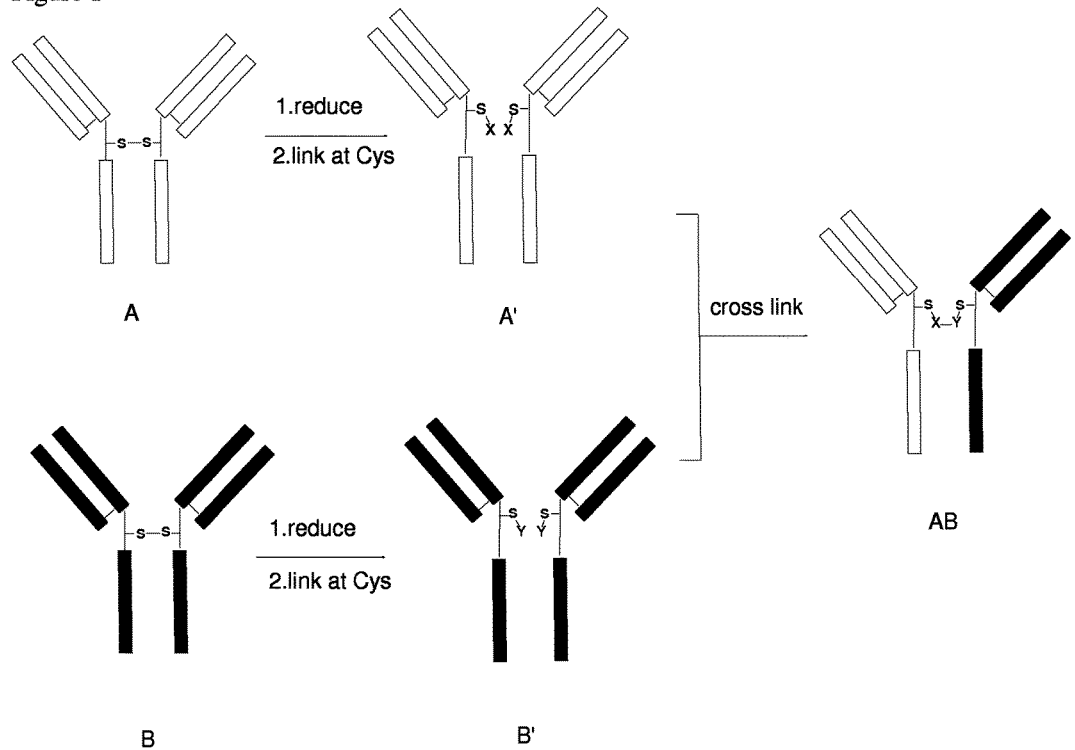
FIG. 1 shows a schematic illustration setting up the generation of bispecific mAb via chemical conjugation to a single Cys residue in the hinge region of an IgG class antibody.

A bispecific antibody (BsAb) is made up of two half-antibody fragments chemically linked at the hinge region (FIG. 1). The starting antibodies are either IgG1 or IgG4 isotypes. The starting antibodies may contain a modified hinge region where a Cys residue is first mutated to a Ser, leaving only one disulfide at hinge. The generation of a bispecific antibody involves three main steps. The first step is a selective reduction of both antibodies A and B to form half antibody fragments. The second step is an introduction of a functional moiety, X or Y, into the hinge region of each antibody half fragment, via a cysteine-based conjugation, leading to a chemically modified antibody fragment halves, A' and B' respectively. In the last step, two antibody fragments halves are linked together, through a chemical ligation between X and Y moieties, to form a bispecific antibody.

The present disclosure provides a process for generation of a chemically-locked bispecific antibody "AB" or "BA" from IgG class antibody "A" and IgG class antibody "B" comprising:

(a) reducing a first antibody "A" with the hinge residue sequence (EU-index numbering: residues 226-229; Kabat numbering: residues 239-242) CPPC (SEQ ID NO.: 1) or CPSC (SEQ ID NO.: 2) or SPPC (SEQ ID NO.: 3) or SPSC (SEQ ID NO.: 4) and a second antibody "B" with the hinge residue sequence (EU-index numbering: residues 226-229; Kabat numbering: residues 239-242) CPPC (SEQ ID NO.: 1) or CPSC (SEQ ID NO.: 2) or SPPC (SEQ ID NO.: 3) or SPSC (SEQ ID NO.: 4) to form half-antibody A and half-antibody-B, wherein antibody A binds to a first target and antibody B binds to a second target, whereby the reducing conditions break any inter-chain or intra-chain disulfide bonds in a hinge region of an class antibody with the hinge residue sequence (residues 226-229) CPPC (SEQ ID NO.: 1) or CPSC (SEQ ID NO.: 2) or SPPC (SEQ ID NO.: 3) or SPSC (SEQ ID NO.: 4);

(b) linking a compound from formula I to one or two Cys residues (EU-index numbering: residues 226 and 229; Kabat numbering: residues 239 and 242) of the hinge core sequence of half-antibody A to form a linked half-antibody A having a structure selected from the group consisting of:

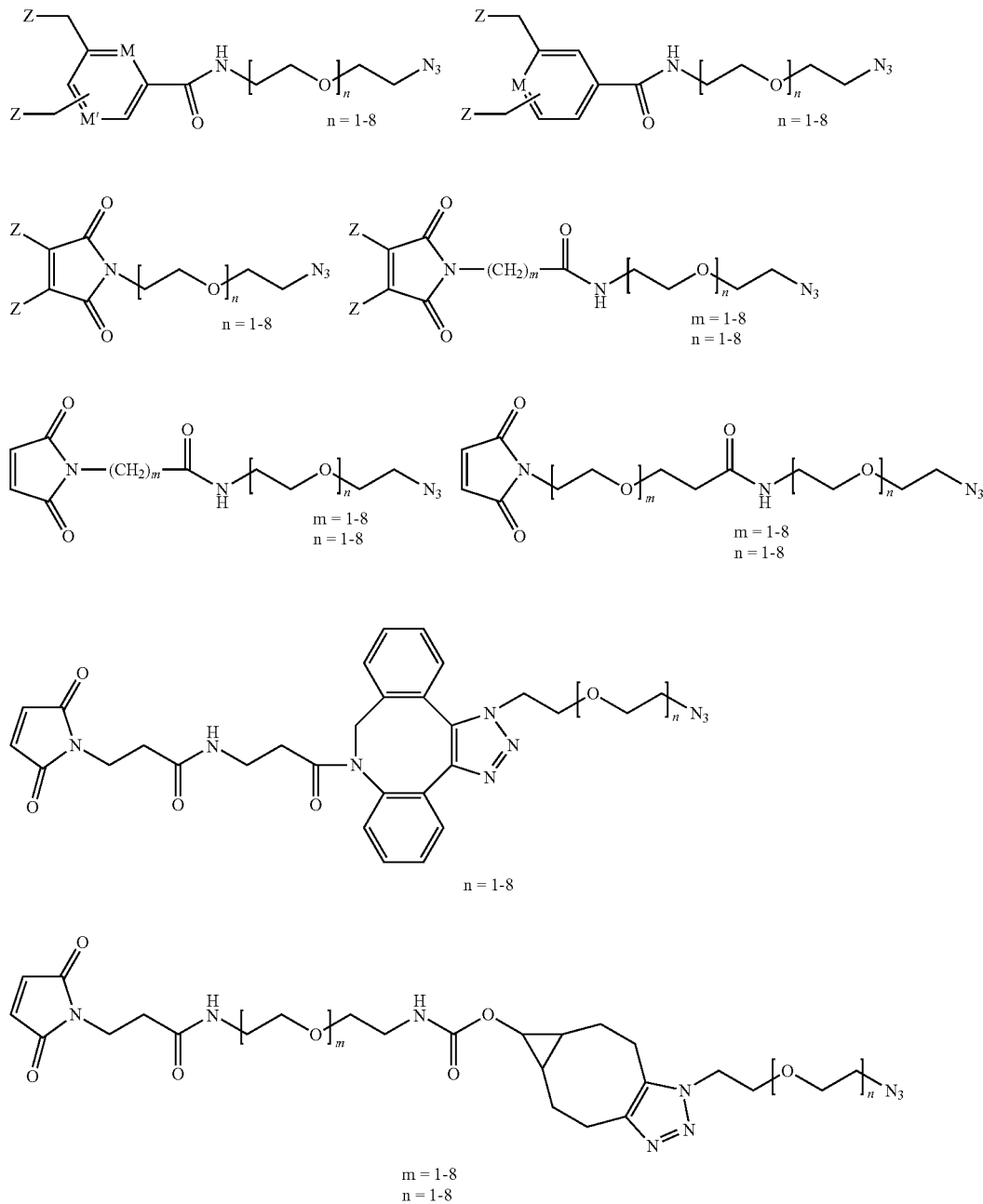

wherein $N_3$ is —N=N=N;

(c) linking a compound from formula II to one or two Cys residues (EU-index numbering: residues 226 and 229; Kabat numbering: residues 239 and 242) of the hinge core sequence of antibody B to form a linked antibody B having the structure selected from the group consisting of:
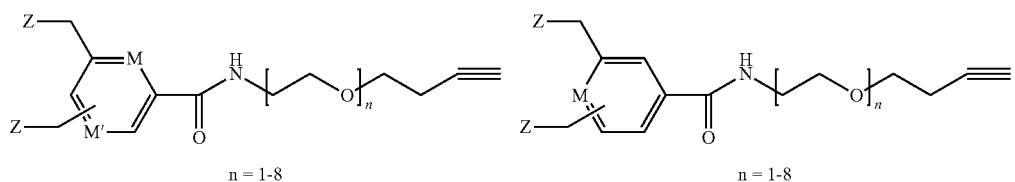
n = 1-8
n = 1-8
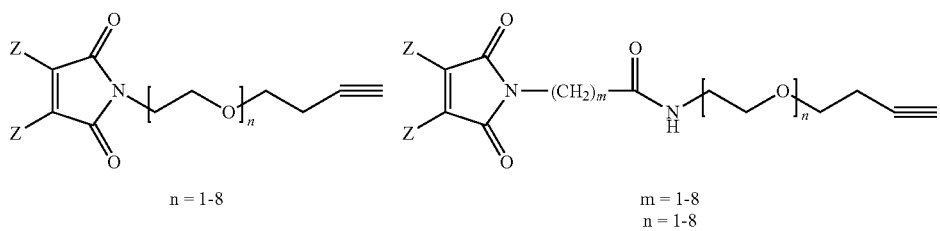
n = 1-8
m = 1-8
n = 1-8
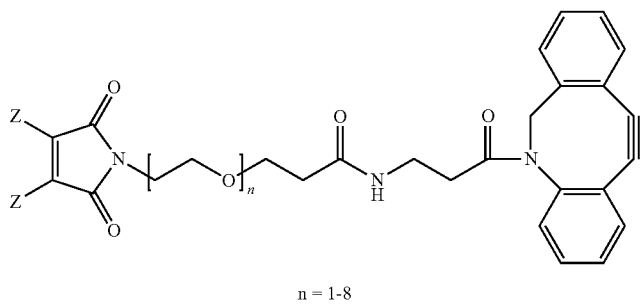
n = 1-8
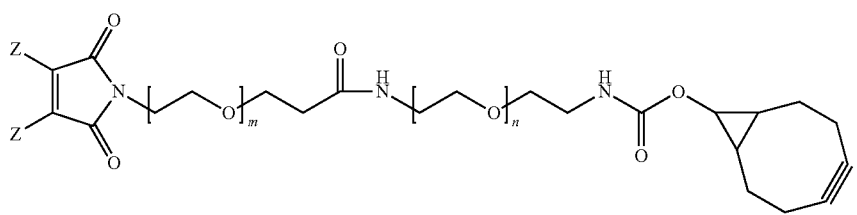
m = 1-8
n = 1-8
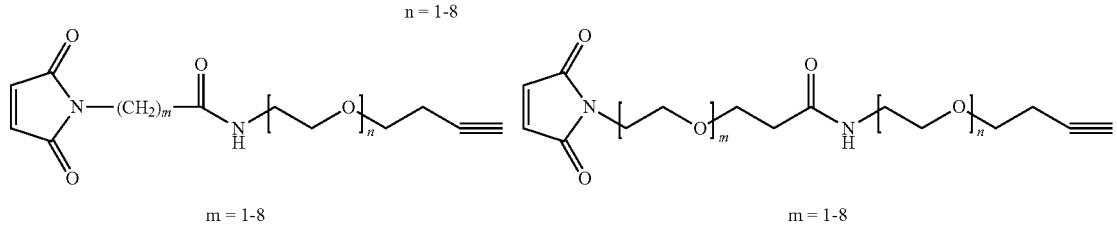
m = 1-8
n = 1-8
m = 1-8
n = 1-8
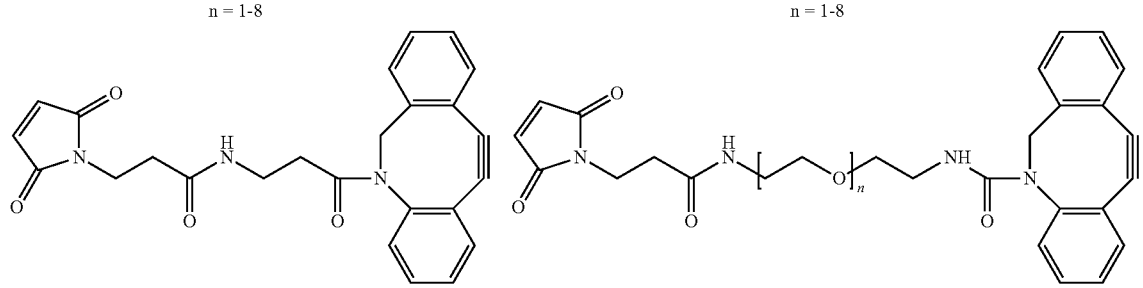
M = N, C
M' = N, C
Z = I, Br, SPh;
n = 1-8 and (d) incubating approximately equal molar amounts of linked antibody A with linked antibody B under neutral conditions to form the bispecific antibody AB that are linked.

Preferably, the reduction of antibody A to form half-antibody A and antibody B to form half-antibody B is conducted in a reducing agent, such as L-cysteine, dithiothreitol, beta-mercapto ethanol, cysteamine, TCEP (tris(2-carboxyethyl)phosphine), 2-MEA (2-Mercaptoethylamine), and combinations thereof. Preferably the hinge region of antibody A, having two Cys residues, is linked with a moiety A having the structure selected from the group consisting of:

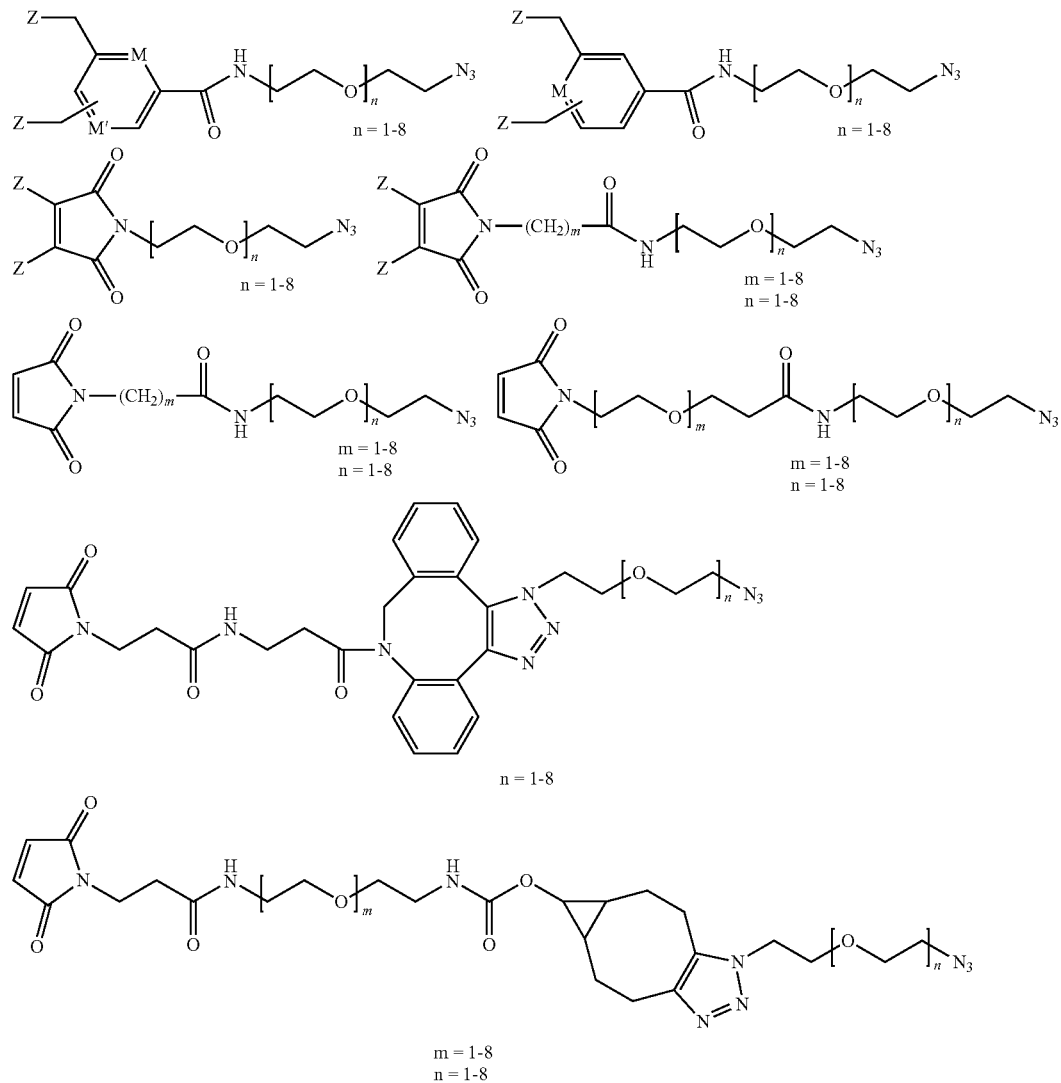

M = N, C
M' = N, C
Z = I, Br, SPh wherein $N_3$ is —N=N=N. Preferably the hinge region of antibody B, having two Cys residues, is linked with a moiety B having the structure selected from the group consisting of:

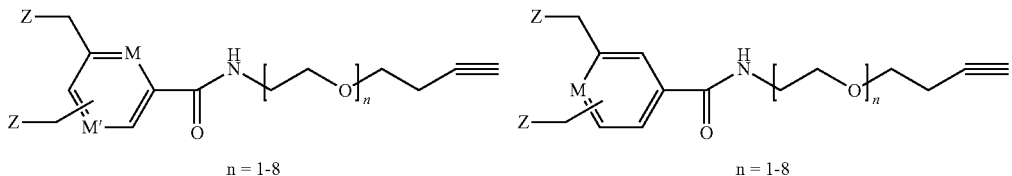

-continued
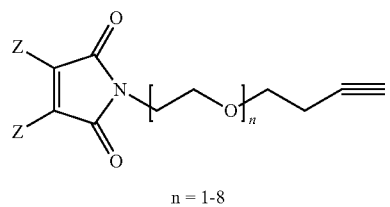
n = 1-8
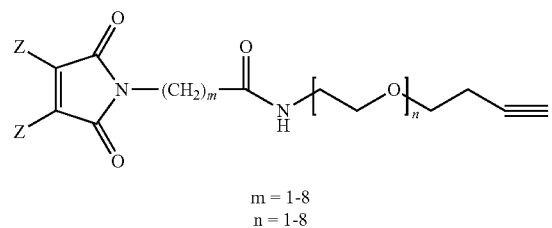
m = 1-8
n = 1-8
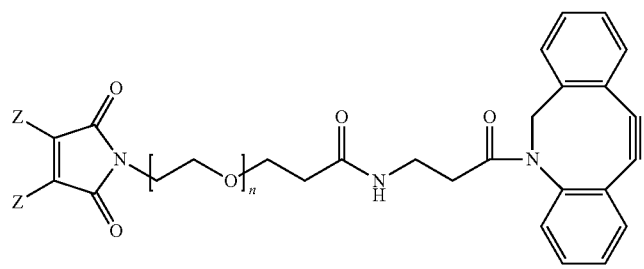
n = 1-8
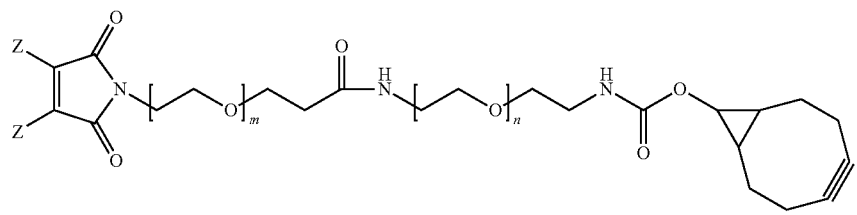
m = 1-8
n = 1-8
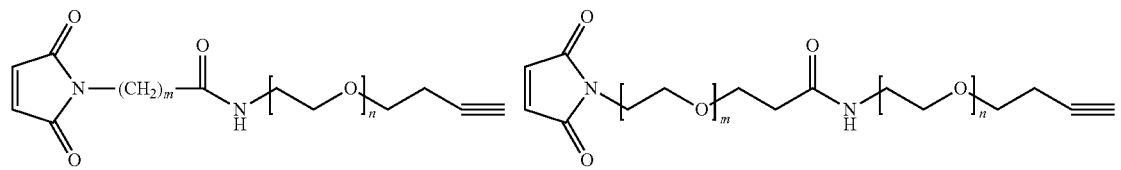
m = 1-8
n = 1-8
m = 1-8
n = 1-8
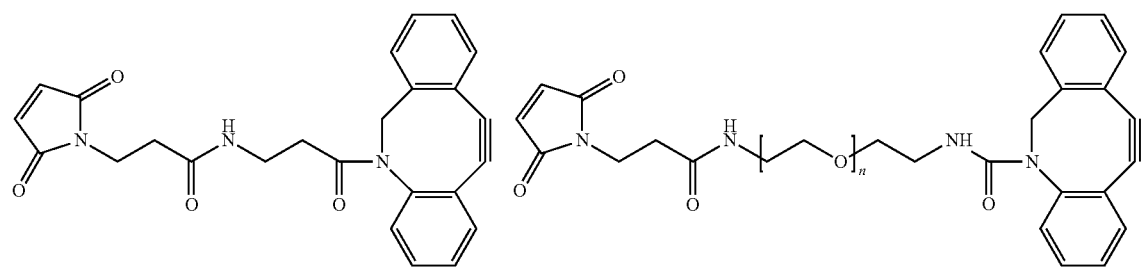
n = 1-8
M = N, C
M' = N, C
Z = I, Br, SPh The present disclosure further provides a chemically-locked bispecific antibody AB, wherein a linked half-antibody A

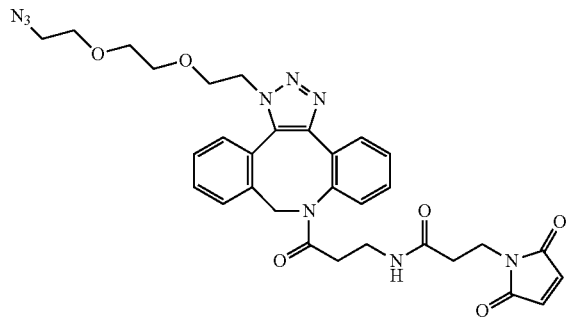

wherein N₃ is —N=N=N;

joins a linked antibody B

Figure 10:
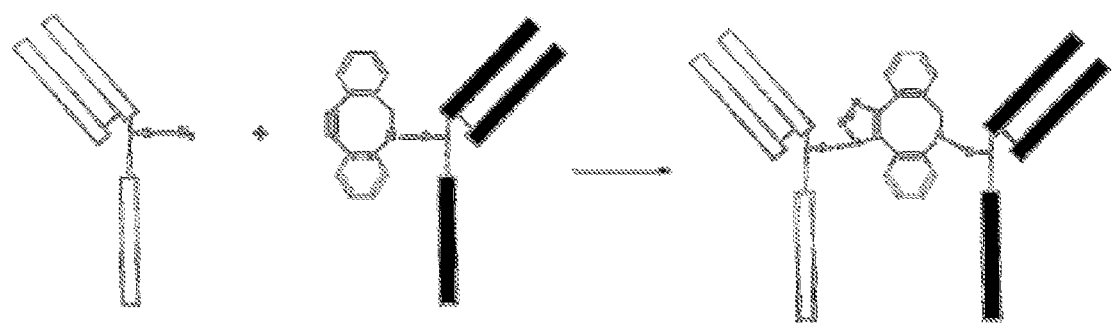
FIG. 10 shows generation of a bispecific antibody via Click conjugation between two half-antibody fragments.

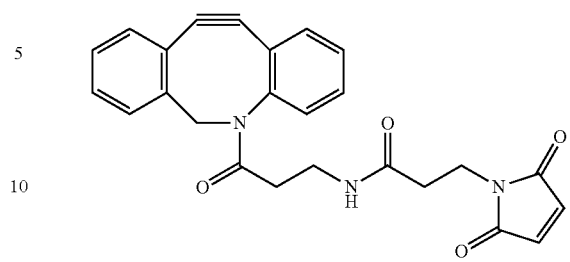

to form a bispecific antibody AB having the structure shown in FIG. 10.

The present disclosure provides a chemically-locked bispecific antibody "AB" or "BA" from IgG class antibody "A" and IgG class antibody "B" comprising a half-antibody A having a structure selected from the group consisting of:

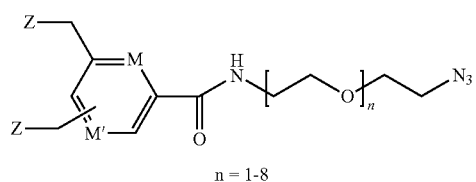

n = 1-8

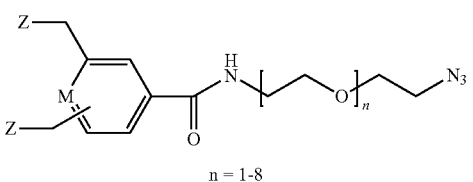

n = 1-8

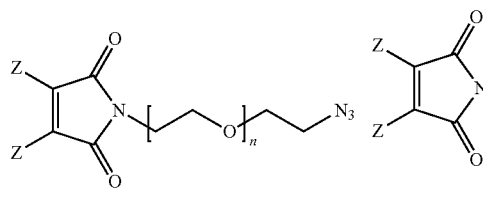

n = 1-8 m = 1-8
n = 1-8

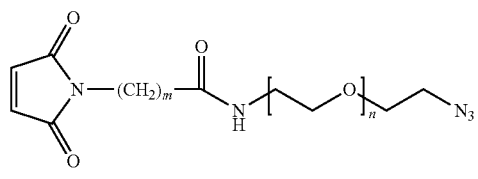

m = 1-8
n = 1-8 m = 1-8
n = 1-8

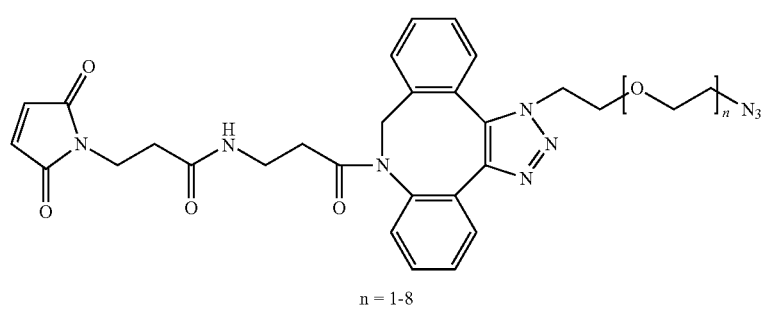

n = 1-8

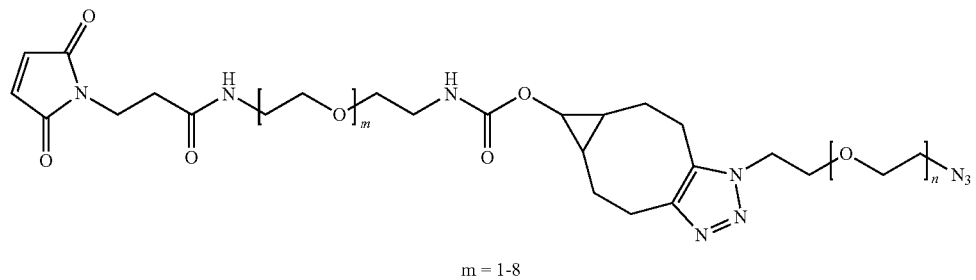
m = 1-8
n = 1-8
M = N, C
M′ = N, C
Z = I, Br, SPh
wherein $N_3$ is —N=N=N;
and a half-antibody B having the structure selected from the group consisting of:
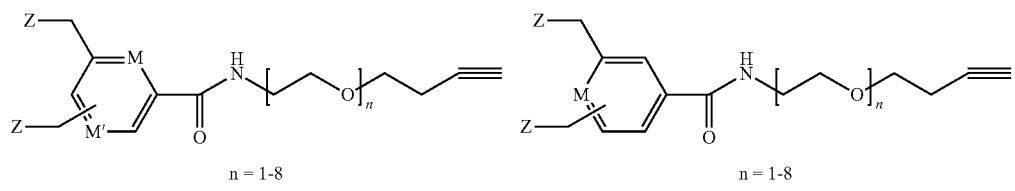
n = 1-8
n = 1-8
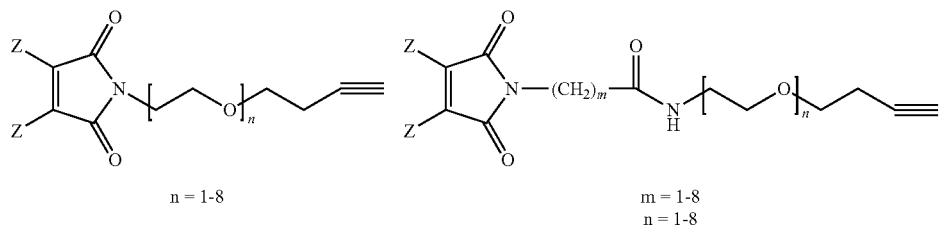
n = 1-8
m = 1-8
n = 1-8
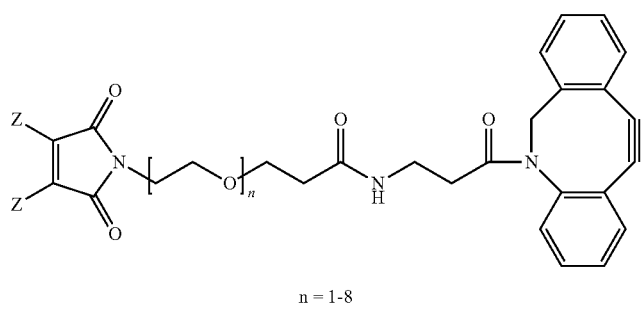
n = 1-8
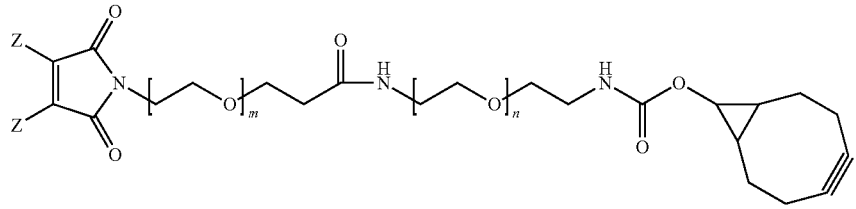
m = 1-8
n = 1-8

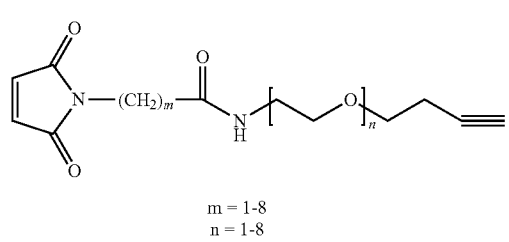
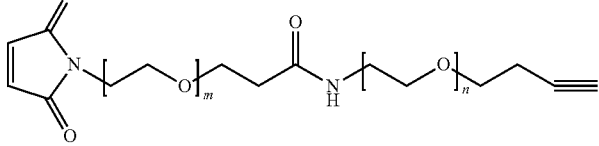

m = 1-8
n = 1-8 m = 1-8
n = 1-8

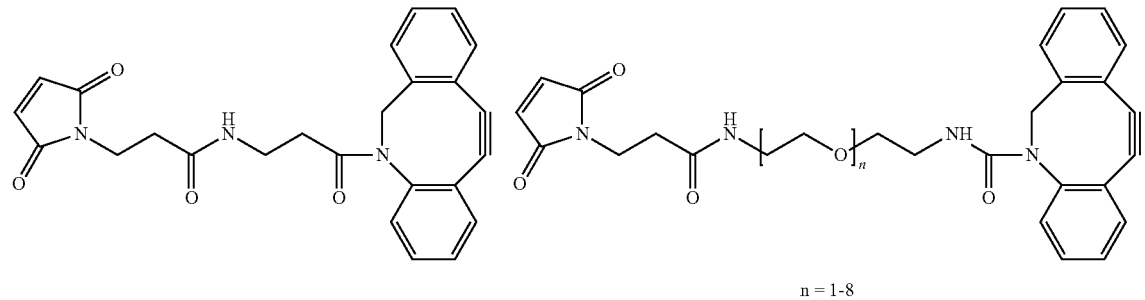

n = 1-8

M = N, C
M' = N, C
Z = I, Br, SPh.

Preferably, the reduction of antibody A to form half-antibody A and antibody B to form half-antibody B is conducted in a reducing agent such as L-cysteine, dithiothreitol, beta-mercapto ethanol, cysteamine, TCEP (tris(2-carboxyethyl)phosphine), 2-MEA (2-Mercaptoethylamine), and combinations thereof.

Preferably, antibodies A and B are monoclonal antibodies. Monoclonal antibodies may be produced by hybridoma methods or by recombinant DNA and protein expression methods. Further, antibodies A and B are full-length antibodies or are antibody fragments.

The antibodies A and B have a CPPC (SEQ ID NO.: 1) core hinge region sequence or a CPSC (SEQ ID NO.: 2) core hinge region sequence or a SPPC (SEQ ID NO.: 3) core hinge region sequence or a SPSC (SEQ ID NO.: 4) core hinge region sequence (EU-index numbering: residues 226-229; Kabat numbering: residues 239-242). Further, step (d) incubating further comprises the step of adding a reducing agent, wherein the reducing gent is selected from the group consisting of L-cysteine, dithiothreitol, beta-mercapto ethanol, cysteamine, TCEP (tris(2-carboxyethyl)phosphine), 2-MEA (2-Mercaptoethylamine), and combinations thereof.

The quality and purity of the resulting bispecific antibodies can be analyzed using routine biochemical techniques, such as absorbance measurements, HP-SEC, SDS-PAGE, native PAGE, and RP-HPLC. It should be noted that the disclosed method generally avoids any purification step because of the specificity of the affinity the linker of formula I for the linker of formula II. However, there are various purification steps provided in US2010/0105874, the disclosure of which is incorporated by reference herein.

The disclosed process further comprises the step of formulating the bispecific antibody for therapeutic use. This is accomplished by a formulation of an effective amount of a bispecific antibody in an aqueous solution that is suitable for human use, in particular suitable for parenteral or intravenous administration.

Figure 2:
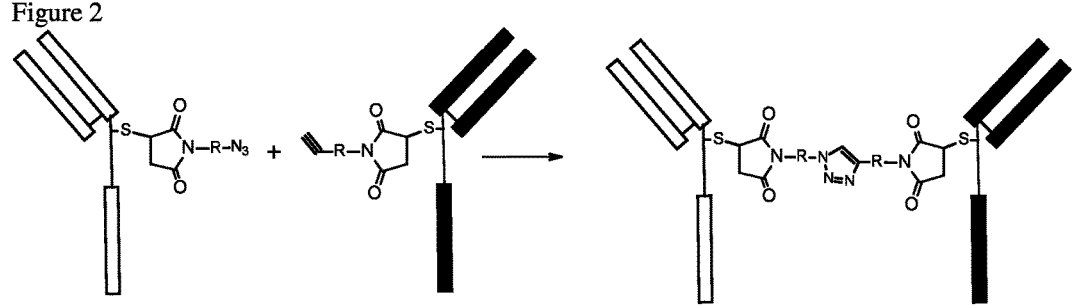
FIG. 2 shows a schematic representation of inter-chain cross-link via chemical conjugation to a single Cys residue in the hinge region of an IgG class antibody according to the disclosure herein.

FIG. 2 shows a scheme to generate bispecific monoclonal antibody (mAb) via chemical conjugation. A bispecific mAb described herein is made up of two half-antibody fragments chemically linked at the hinge region. The process of bispecific mAb generation involves three main steps (FIG. 2). The first step is a selective reduction of hinge disulfides in two different mAb A and B respectively. The second step is an induction of intrachain-link between two cysteines on the same heavy chain in each mAb through a linker X or Y. The intrachain-link process produces two chemically locked mAb fragments A' and B'. In the last step, two mAb fragments are linked together through a chemical ligation between X and Y to form a bispecific antibody AB.

IgG1 with hinge mutations (CPSC; SEQ ID NO.: 2), wt IgG4 and IgG4 with hinge mutations (SPSC; SEQ ID NO.: 4) were used in this study.

The first step is to reduce each of antibody A and antibody B. In one embodiment, the antibody (10 mg) was treated with 10 molar equivalents of 2-mercaptoethyl-amine (2-MEA) in 0.1M PBS pH 7.4, 1.0 mM diethylenetriaminepentaacetic acid (DTPA) for 2 h at 37° C. Excess 2-MEA was purified away from the partially reduced mAb using 50 kDa filter centrifuge tubes with centrifugation conducted at 3,000 RPM for 20 minutes. A total of three washes with 0.1M PBS were conducted. The protein concentration was quantified using an absorbance value of 1.58 at 280 nm for a 1.0 mg/mL solution, and the molar concentration determined using a molecular weight of 150,000 g/mol.

In another embodiment of the reduction step, the antibody (10 mg) was treated with 3.0 molar equivalents of dithiothreitol (DTT) in 0.1M PBS pH 7.4, 1.0 mM diethylenetriaminepentaacetic acid (DTPA) for 2 h at 24° C. The excess DTT was purified away from the partially reduced mAb using 50 kDa filter centrifuge tubes with centrifugation conducted at 3,000 RPM for 20 minutes. A total of 3 washes with 0.1M PBS were conducted.

In another embodiment of the reduction step, the mAb (10 mg) was treated with 2.0 molar equivalents of tris (2-carboxyethyl)-phosphine (TCEP) in 0.1M PBS pH 8.0, 1.0 mM diethylenetriaminepentaacetic acid (DTPA) for 2 h at 24° C. The mAb concentration was 8.0 mM. Without purification, the partially reduced mAb was used in conjugation step directly.

Figure 3:
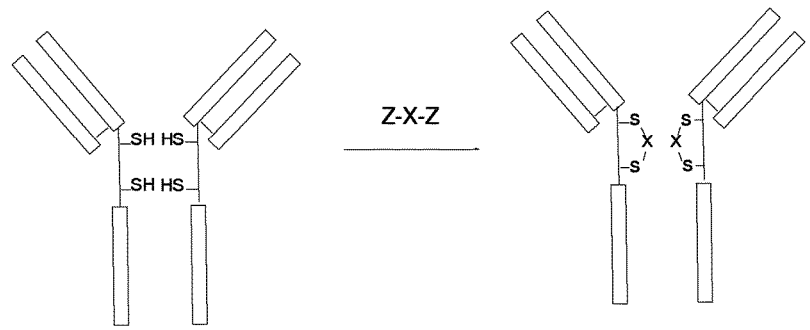
FIG. 3 shows a schematic representation of an intra-chain cross link to two Cys residues within the hinge region of an IgG class antibody.
Figure 4:
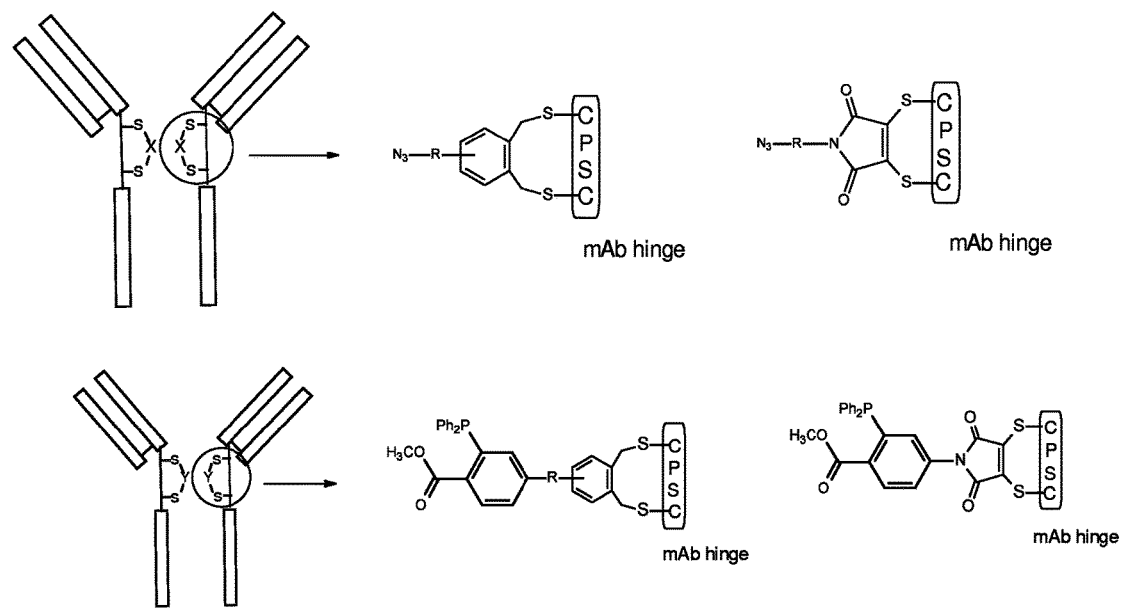
FIG. 4 shows (top and bottom) a schematic representation for generation of bispecific mAb via inter-chain cross linking to two Cys residues within the hinge region (CPSC, SEQ ID NO.: 2) of an IgG class antibody
Figure 5:
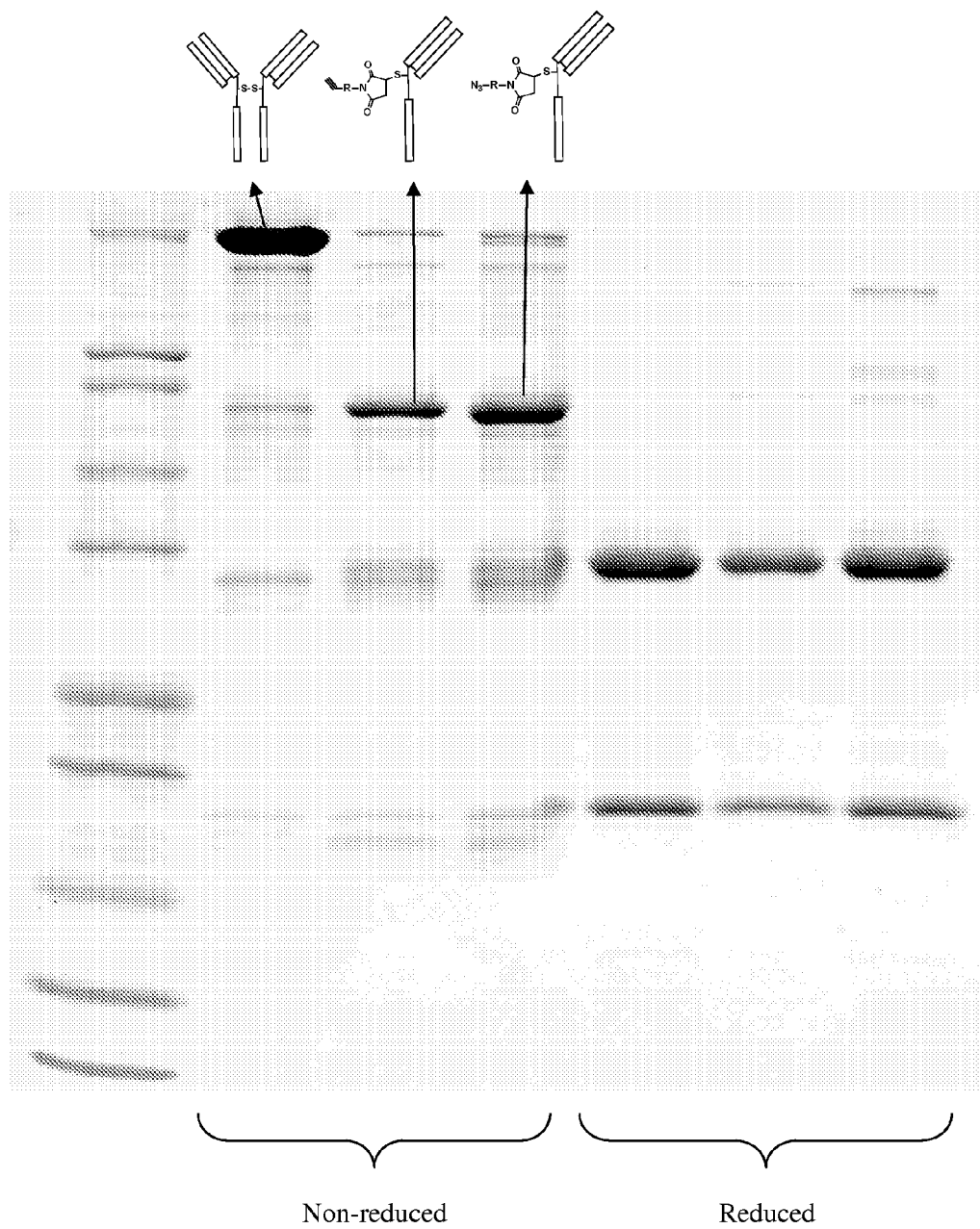
FIG. 5 shows an SDS PAGE analysis of chemically locked half-mAb fragments.
Figure 6:
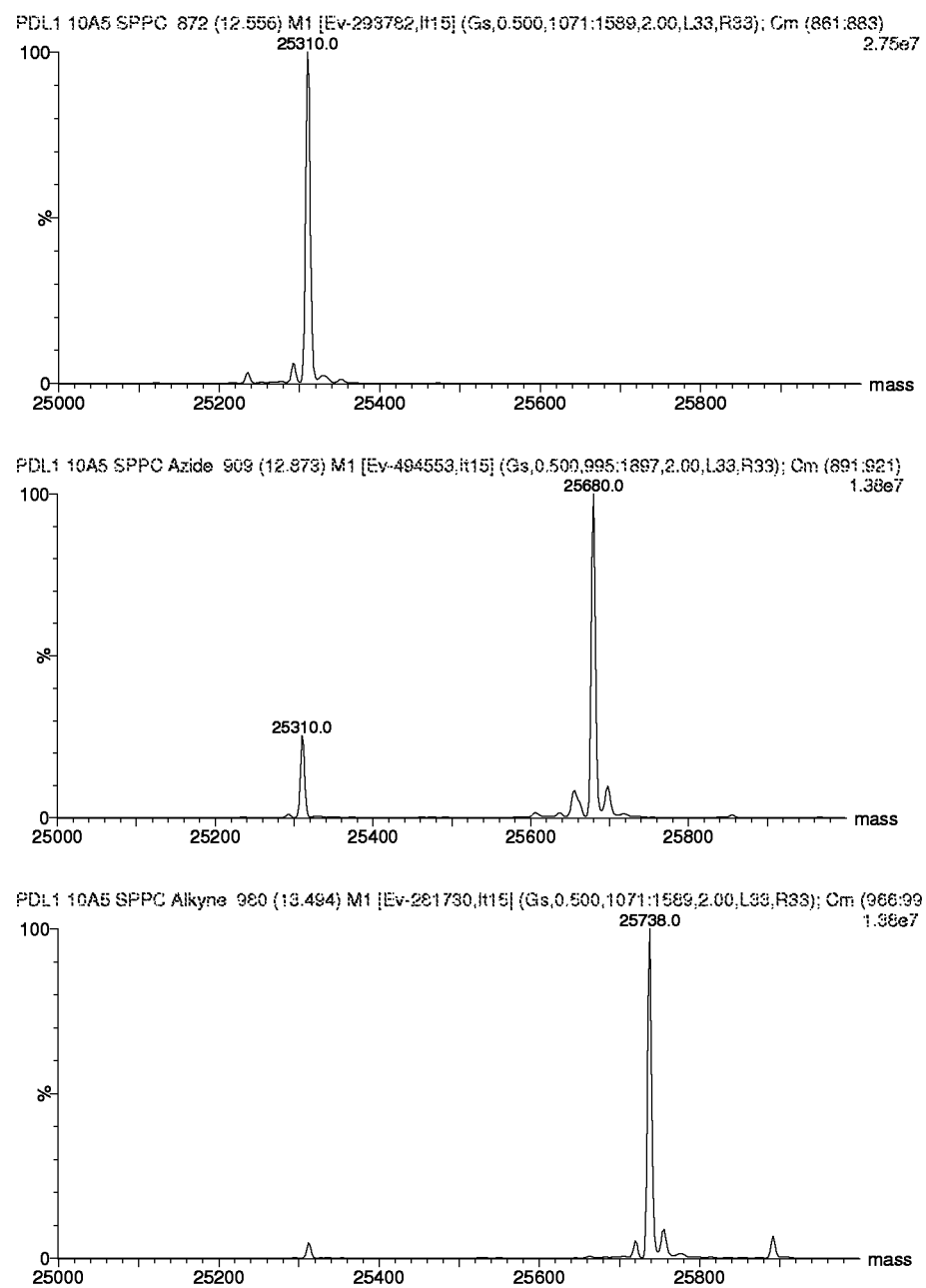
FIG. 6 shows an MS analysis of HC Fab from naked mAb(top), azide-conjugated mAb fragment (middle) and alkyne-conjugated mAb fragment (bottom).
Figure 7:
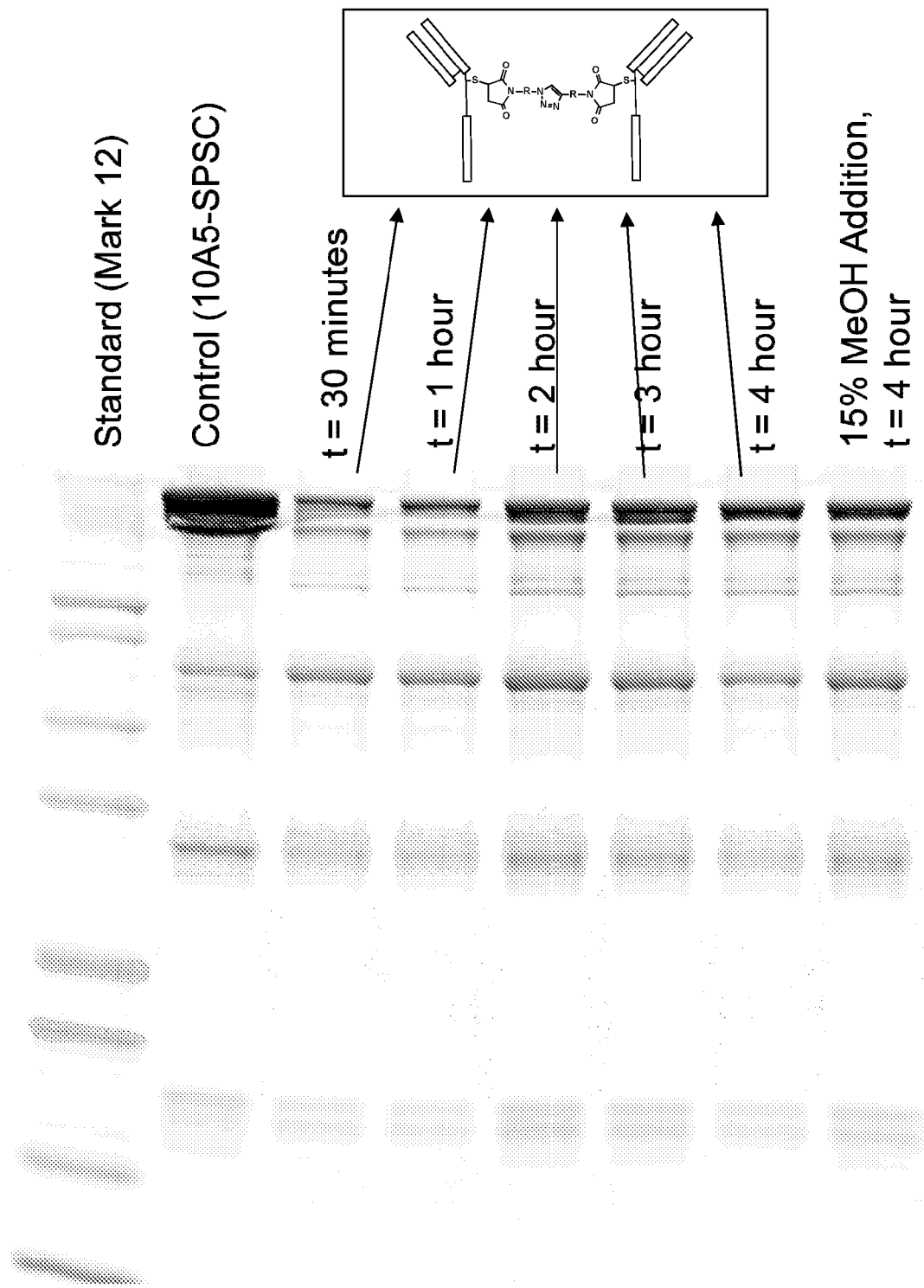
FIG. 7 shows SDS PAGE of cross-link products from azide-attached half mAb and alkyne-attached half mAb fragments.

The second step is the conjugation step. A partially reduced mAb "Antibody A" from a reduction step in 0.1M PBS was added to 2.5 molar equivalents of cross linking agent Z—X—Z (FIG. 2 and FIG. 3). The cross linking agent was taken from a pre-prepared stock solution in DMSO (1 mg/mL). In the reaction mixture, partially reduced antibody concentration was 8.0 mg/mL and DMSO content was 5% (v/v). The conjugation was carried out for 2 hr at 24° C. Cysteine (1 mM final) was used to quench any unreacted, excess cross linking agents. Conjugated mAb was purified using PD-10 columns equilibrated with phosphate buffered saline. The conjugated mAb structures are illustrated in FIG. 4. Under the same conditions, second mAb (Antibody B) was conjugated with crossing linking agent Z—Y—Z (FIG. 5 and FIG. 6) and purified. The conjugated mAb structures are illustrated in FIG. 7 and FIG. 8.

Figure 9:
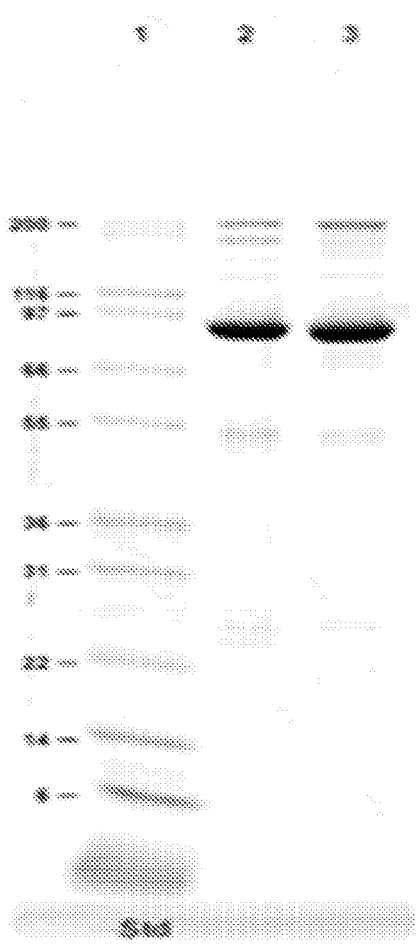
FIG. 9 shows non-reduced SDS PAGE of chemically modified half antibody fragments (lane 2 and 3) produced in Example 4 herein.

The third step is the inter-chain conjugation step. The click conjugation for interchain cross-link is illustrated in FIG. 9. In brief, to azide-decorated antibody fragments (3.0 mg) in 0.5 mL of PBS (0.1M, pH 7.4) is added 3.0 mg of alkyne-decorated antibody fragments in 0.5 mL of PBS (0.1M, pH 7.4). To this mixture is added 50 µL of acetonitrile and the final content of acetonitrile is 5% (v/v). After 3 hr of reaction at room temperature, the mixture is purified using 100 kDa filter centrifuge tubes with centrifugation conducted at 3,000 RPM for 20 minutes. The mixture is washed with PBS for 3 times and the resulted product is subject to in vitro characterization.

Example 1

This example shows the synthesis of a bispecific antibody according to the disclosed process. FIG. 4 shows a scheme to generate bispecific monoclonal antibody (mAb) by chemical conjugation to two Cys residues in the hinge region of an IgG class antibody. The disclosed bispecific mAbs are made up of two half-antibody fragments chemically linked at their respective hinge regions. The process to synthesize bispecific mAbs involves three main steps shown in FIG. 5. The first step is a selective reduction of hinge disulfides in two different mAb's, A and B respectively. The second step is an induction of intrachain-link between two cysteines on the same heavy chain in each mAb through a linker X or Y. The intrachain-link process produces two chemically locked mAb fragments A' and B'. In the last step, two mAb fragments are linked together through a chemical ligation between X and Y to form a bispecific antibody AB.

More specifically, we obtained antibody "A" an IgG1 with hinge mutations (CPSC; SEQ ID NO.: 2) and antibody "B" a wild type IgG4. The first step was antibody reduction. Condition 1: The antibodies (10 mg) were separately treated with 10 molar equivalents of 2-mercaptoethyl-amine (2-MEA) in 0.1M PBS pH 7.4, 1.0 mM diethylenetriaminepentaacetic acid (DTPA) for 2 h at 37° C. Excess 2-MEA was purified away from the partially reduced mAb using 50 kDa filter centrifuge tubes with centrifugation conducted at 3,000 RPM for 20 minutes. A total of three washes with 0.1M PBS were conducted. The protein concentration was quantified using an absorbance value of 1.58 at 280 nm for a 1.0 mg/mL solution, and the molar concentration determined using a molecular weight of 150,000 g/mol.

Condition 2: The antibody (10 mg) was treated with 3.0 molar equivalents of dithiothreitol (DTT) in 0.1M PBS pH 7.4, 1.0 mM diethylenetriaminepentaacetic acid (DTPA) for 2 h at 24° C. The excess DTT was purified away from the partially reduced mAb using 50 kDa filter centrifuge tubes with centrifugation conducted at 3,000 RPM for 20 minutes. A total of 3 washes with 0.1M PBS were conducted.

Condition 3: The mAb (10 mg) was treated with 2.0 molar equivalents of tris (2-carboxyethyl)-phosphine (TCEP) in 0.1M PBS pH 8.0, 1.0 mM diethylenetriaminepentaacetic acid (DTPA) for 2 h at 24° C. The mAb concentration was 8.0 mM. Without purification, the partially reduced mAb was used in conjugation directly.

Example 2

This example shows that the bispecific antibody made in Example 1 retained both of its original half Mab binding characteristics.

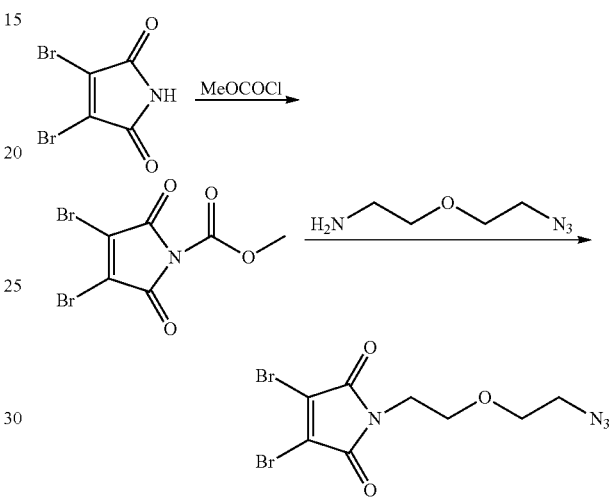

Synthesis of 1-(2-(2-azidoethoxy)ethyl)-3,4-dibromo-1H-pyrrole-2,5-dione

To 2.5 g of 3,4-dibromo-1H-pyrrole-2,5-dione (10 mmol) and 1 g of NMM in 60 mL of THF, MeOCOCl (10 mmol, 940 mg in 10 ml DCM) was added dropwise, stirred for 20 min, then the reaction solution was diluted with 6o mL of DCM, washed 3 time by water, the organic phase was stirred by sodium sulfate anhydrous, concentrated, 2.65 g of methyl 3,4-dibromo-2,5-dioxo-2H-pyrrole-1(5H)-carboxylate was obtained. To 311 mg, 1 mmol of this compound, 2-(2-azidoethoxy)ethanamine (130 mg, 1 mmol) and 5 mL DCM was added, TLC shown the reaction finished in 20 min, then extracted by DCM and brine, washed by NH$_4$Cl solution, dried on sodium sulfate anhydrous, and then concentrated for column purification, flashed by 2:1 hexane and ethyl ethylate, 230 mg of 1-(2-(2-azidoethoxy)ethyl)-3,4-dibromo-1H-pyrrole-2,5-dione obtained. $^1$HNMR: 3.32 ppm (t, J=5.0 Hz, 1H), 3.40 ppm (t, J=5.0 Hz, 1H), 3.50 ppm (q, J=5.0 Hz, 1H), 3.62 ppm (t, J=5.0 Hz, 1H), 3.63-3.69 ppm (m, 3H), 3.84 ppm (t, J=5 hz, 1H). Fw: 365.9, $C_8H_8Br_2N_4O_3$; Mass Peaks (1:2:1): 366.9, 368.9, 370.9.

Example 3

This example illustrates chemical generation of a bispecific antibody using a single Cys residue located in the hinge region of an IgG class antibody. The starting mAbs described herein contain an engineered hinge region where one Cys at the same position on each chain was mutated to Ser, thus resulting in a hinge with only a single disulfide left. The process of bispecific mAb generation involves three main steps (FIG. 1). The first step is a selective reduction of hinge disulfide in two different mAb A and B respectively. The second step is an induction of a functional moiety X or Y via a cysteine-based conjugation. The Cys-link step produces two chemically locked mAb fragments A' and B'. In the last step, two mAb fragments are linked together through a chemical ligation between X and Y to form a bispecific antibody AB. An IgG1 monoclonal antibody with a hinge region mutation (SPPC; SEQ ID NO.: 3) were used in this study.

Condition 1: The antibody (10 mg) was treated with 10 molar equivalents of 2-mercaptoethyl-amine (2-MEA) in 0.1M PBS pH 7.4, 1.0 mM diethylenetriaminepentaacetic acid (DTPA) for 2 h at 37° C. Excess 2-MEA was purified away from the partially reduced mAb using 50 kDa filter centrifuge tubes with centrifugation conducted at 3,000 RPM for 20 minutes. A total of three washes with 0.1M PBS were conducted. The protein concentration was quantified using an absorbance value of 1.58 at 280 nm for a 1.0 mg/mL solution, and the molar concentration determined using a molecular weight of 150,000 g/mol.

Condition 2: The antibody (10 mg) was treated with 3.0 molar equivalents of dithiothreitol (DTT) in 0.1M PBS pH 7.4, 1.0 mM diethylenetriaminepentaacetic acid (DTPA) for 2 h at 24° C. The excess DTT was purified away from the partially reduced mAb using 50 kDa filter centrifuge tubes with centrifugation conducted at 3,000 RPM for 20 minutes. A total of 3 washes with 0.1M PBS were conducted.

Condition 3: The mAb (10 mg) was treated with 2.0 molar equivalents of tris (2-carboxyethyl)-phosphine (TCEP) in 0.1M PBS pH 8.0, 1.0 mM diethylenetriaminepentaacetic acid (DTPA) for 2 h at 24° C. The mAb concentration was 8.0 mM. Without purification, the partially reduced mAb was used in conjugation directly.

Example 4

This example shows methods for making bispecific antibodies, according to the disclosed process herein and having the disclosed chemical linking structure linking the hinge regions of each half antibody fragment to each other. The antibody scaffolds were: IgG4 with a hinge mutation (SPSC, SEQ ID NO.: 4).

We first modified each Ig antibody to generate a half antibody through a chemical modification. Specifically, a buffer exchange reaction added antibody (0.5-3 mg) to a 15 mL filter centrifuge tube (Millipore, UFC903024) and added an appropriate volume of a pH 8.0 PBS 1 mM DTPA (diethylene triamine pentaacetic acid) buffer to the 50 mL mark on the tube. The tube was centrifuged at 3,000 RPM for 20 minutes at 5° C. The antibody was transferred into a 1.5 mL plastic vial and check concentration using the Nanodrop (Fisher, ND-2000 UV-Vis Spectrophotometer). The final antibody concentration was between 5-8 mg/mL.

A stock solution of 1 mg/mL TCEP ((tris(2-carboxyethyl) phosphine)), Sigma-Aldrich, C4706) in pH 8.0 PBS (1.0 mM DTPA) buffer was prepared. We used the following table to calculate the volume of the TCEP solution that needed to be added to the antibody, depending on the number of equivalents and resulting mass of antibody recovered after buffer exchange.

| Sample | MW | Equivalents | Concentration (mmol) | Mass (mg) | Volume (mL) | Concentration (mg/mL) |
|---|---|---|---|---|---|---|
| Antibody | 150000 | 1 | 2.74E−06 | 1 | 0.2 | 5 |
| TCEP | 286 | 3 | 0.00002 | 0.0057 | | |
| DBCO | 427 | 5 | 3.33E−05 | 0.014233 | 0.01 | 1.4233 |

An appropriate volume of the TCEP solution (calculated by the above-table, was added to the antibody solution, vortexed lightly and the vial was placed on a carousel. The reduction reaction was conducted for 90 minutes at room temperature.

A stock solution of DBCO-maleimide (Click Chemistry Tools, A108-100) in DMSO (Sigma-Aldrich, 472301) was prepared based on the calculation from the table above. The DBCO-maleimide in DMSO was added to the antibody sample (without purification of TCEP). Final volume of DMSO in antibody sample was about 5% (v/v). The conjugation reaction was conducted for 1 hour at room temperature under mixing by carousel. Each sample was placed into a separate 15 mL filter centrifuge tube (Millipore, UFC903024) and added an appropriate volume of 1×DPBS (Corning, 21-031-CM, no calcium or magnesium) buffer to the 50 mL mark on the tube. The samples were centrifuged at 3,000 RPM for 20 minutes at 5° C. The wash step was repeated once more. After wash, the samples was transferred into separate 1.5 mL plastic vials and placed in refrigerator (5° C.).

For IgG4 antibodies, 4.0 equivalents of TCEP had provided a large amount of half-antibody. For IgG1 antibodies, 3.5 equivalents of TCEP had provided a large amount of half-antibody. 5.0 equivalents of DBCO was used for both types of antibodies.

To a solution of DBCO-maleimide (1.0 mg, 1.0 equivalent) in DMSO (0.12 mL) was added azido-PEG4-azide (2.5 mg, 5.0 equivalent) in DMSO (0.6 mL). The mixture was stirred at room for 2 hr. The reaction was completed as indicated by LC/MS. Molecular weight of the resulting azide-maleimide was 627.65 g/mol. Azide-maleimide Synthesis (Scheme 1)

Scheme 1. Synthesis of azide-maleimide

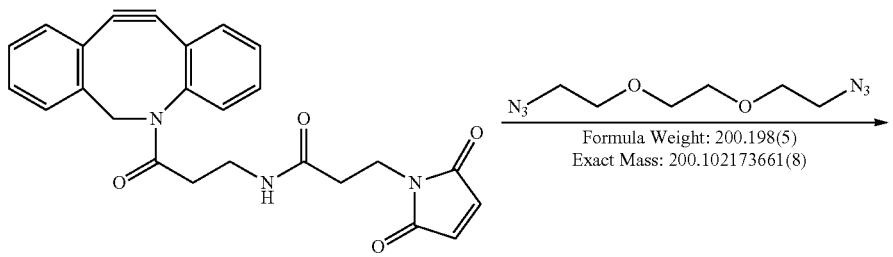

Formula Weight: 427.45(2)
Exact Mass: 427.15320618(1)

Formula Weight: 200.198(5)
Exact Mass: 200.102173661(8)

-continued

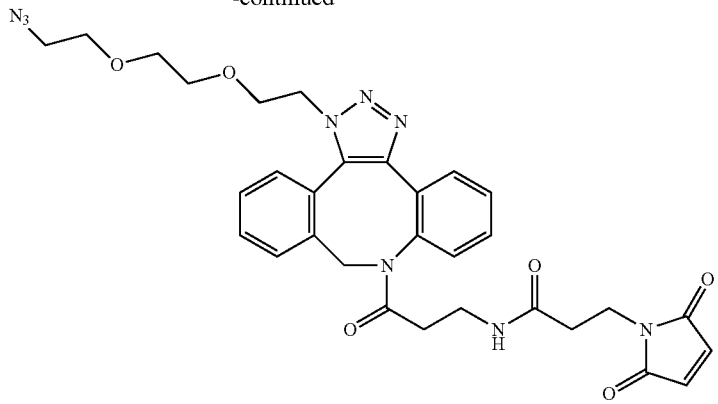

Formula Weight: 627.65(2)
Exact Mass: 627.25537984(2)

The Azide-maleimide (5.0 equivalents) in DMSO was added to the antibody sample. Final volume of DMSO in antibody sample was about 5% (v/v). The conjugation reaction was conducted for 1 hour at room temperature under mixing by carousel. The sample was washed as described previously.

Each half-antibody fragment was purified by a hydrophobic interaction column (HIC). The HIC assay was conducted with a TOSOH butyl-NPR column at 40° C. column temperature and 0.6 mL/min flow rate. Elution was achieved with a 30 min gradient of decreasing salt concentration (from 1.5 to 0 M ammonium sulfate) and increasing organic modifier (from 0% to 25% isopropyl alcohol) in a 50 mM Sodium phosphate buffer at pH 7.0. The half-antibody fragment was analyzed by SDS PAGE. Specifically, for each sample to be analyzed, 20 μL at a concentration of 0.6 mg/mL was required. We followed established protocols for running SDS-PAGE gels (RTP AD001-01 and AD002-01). FIG. 9 shows non-reduced SDS PAGE of chemically modified half antibody fragments (lane 2 and 3).

Example 5

Figure 11:
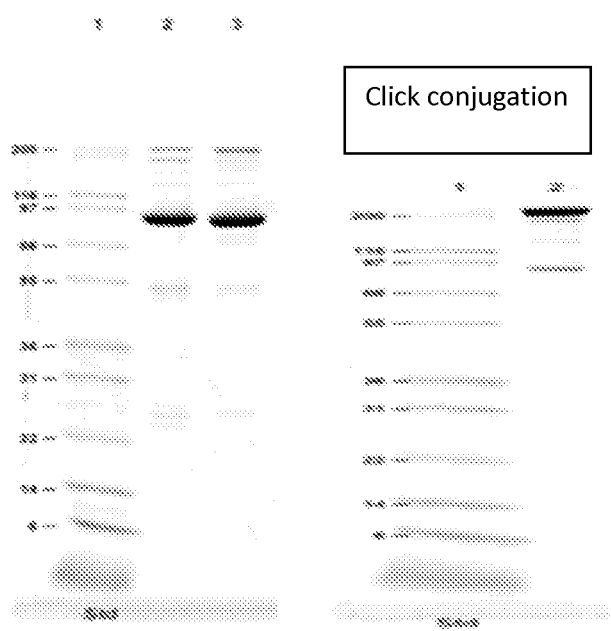
FIG. 11 shows non-reduced SDS PAGE of half-antibody fragments (a) and Click product (b). The half-antibody-azide is in lane 2 in gel (a) and half-antibody-DBCO is lane 3 in gel (a). Click product is in lane 2 in gel (b).

This example illustrates Bispecific antibody generation via a Click reaction. FIG. 10 shows generation of a bispecific antibody via Click conjugation between two half-antibody fragments. A Click reaction between two half-antibody fragments is shown in FIG. 10. To a half-antibody-azide fragment (500 μg) in PBS (5.0 mg/mL) was added half-antibody-DBCO fragment (500 μg) in PBS (5.0 mg/mL). The reaction was conducted for 2 hours at room temperature under mixing by carousel. The mixture was subject to SDS PAGE analysis (FIG. 11) and purification by ion-exchange chromatography.

Figure 12:
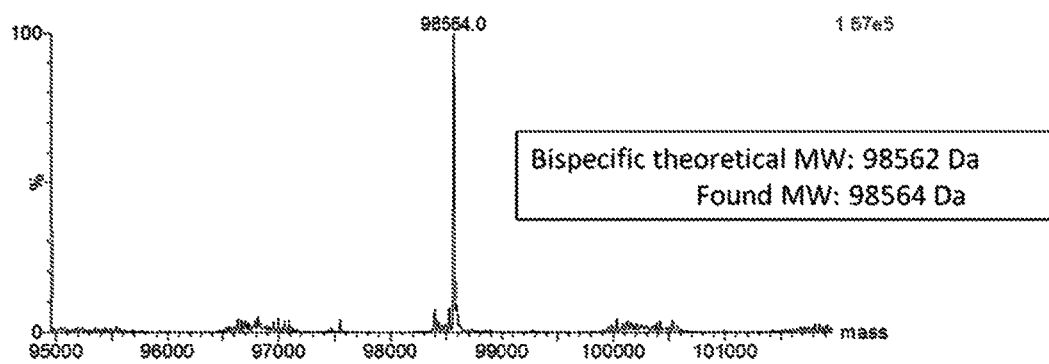
FIG. 12 shows a mass spectrum of IdeS digested Click product showing mass of bispecific antibody CBA-0710.

A bispecific antibody was purified on an Agilent 1200 HPLC using a Thermo WCX-10 column at 0.6 mL/min flow rate. Elution was achieved with a 30 min gradient of increasing salt concentration (from 0 to 100 mM NaCl) in a 10 mM MES buffer at pH 5.7. Bispecific antibody STI CBA-0710 was digested by IdeS protease and analyzed and confirmed on Water Xevo G-2 QTOF mass spectrometry (FIG. 12).

Figure 13:
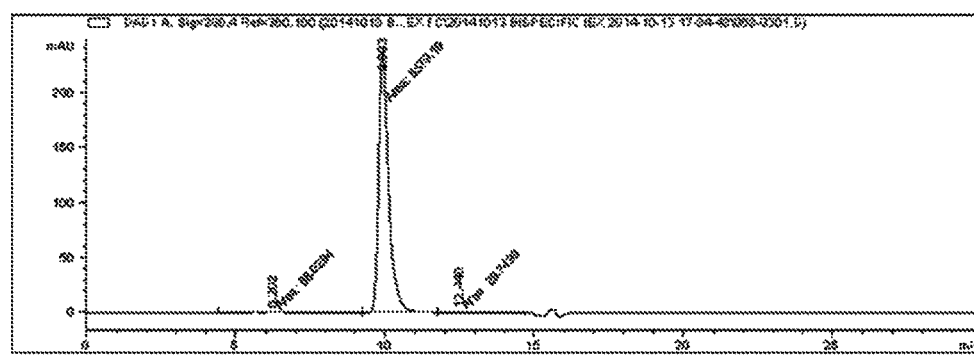
FIG. 13 shows SEC size-exclusion chromatography of bispecific antibody CBA-0710.

The biophysical properties of the bispecific antibody STI CBA-0710 was determined by size-exclusion chromatography (SEC) of bispecific antibody (FIG. 13). Specifically, the bispecific antibody was analyzed on Agilent 1200 HPLC using a TSK gel SuperSW3000 column (4.6 mm IDx30 cm, 4 μm). Buffer was 0.2 M potassium phosphate, 0.25M KCl, pH 6.2.

TABLE 2

SEC data of bispecific antibody CBA-0710

| Main | HMWS | LMWS |
|---|---|---|
| 98.3% | 1.2% | 0.5% |

Figure 14:
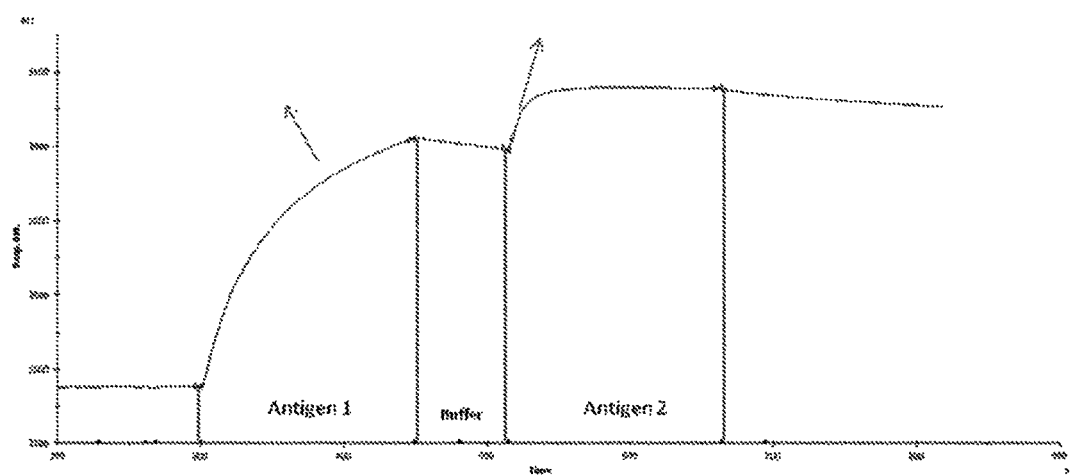
FIG. 14 shows binding of bispecific antibody CBA-0710 on BIAcore. More specifically, FIG. 14 show 2 simultaneous binding of bispecific antibody CBA-0710 to two antigens on BIAcore.

FIG. 14 shows binding of bispecific antibody CBA-0710 on BIAcore. The first antigen was immobilized on CM5 sensor chip to approximately 1500 RU using standard NHS/EDC coupling methodology. Ran buffer for the base line. Loaded bispecific antibody and followed with buffer, then ran binding against the second antigen.

Example 6

This example shows various assay results for the bispecific antibodies produced herein. There are cell-based binding and functions of a bispecific antibody. Bispecific antibody CBA-0710 bound to MDA-MB-231 (human breast cancer) cells (FIG. 15), as assayed by flow cytometry. $EC_{50}$ values for antibodies were determined. MDA-MB-231 triple-negative breast cancer (TNBC) cells expressing both antigen-1 and antigen-2 were harvested with enzyme-free Cell Dissociation Buffer (GIBCO) and transferred to V-Bottom 96 well-plates (50,000 cells/well). Cells were incubated on ice for 45 min with serial dilutions of either the bispecific antibody CBA-0710, or the parental monospecific anti-antigen-1 or anti-antigen-2 antibody in FACS buffer (PBS+2% FBS)+$NaN_3$. After 2 washes in FACS buffer, a 1:1000 dilution of Phycoerythrin conjugated anti-Human IgG (γ-chain specific) was added and incubated for 30 min. Following a final wash, fluorescence intensity was measured on an Intellicyt High Throughput Flow Cytometer (HTFC). Data were analyzed using Graphpad Prism software and non-linear regression fit. Data points are shown as the median fluorescence intensity (MFI) of positively labeled cells +/− Standard Error. $EC_{50}$ values are reported as the concentration of antibody to achieve 50% of maximal binding to the cells.

Figure 15:
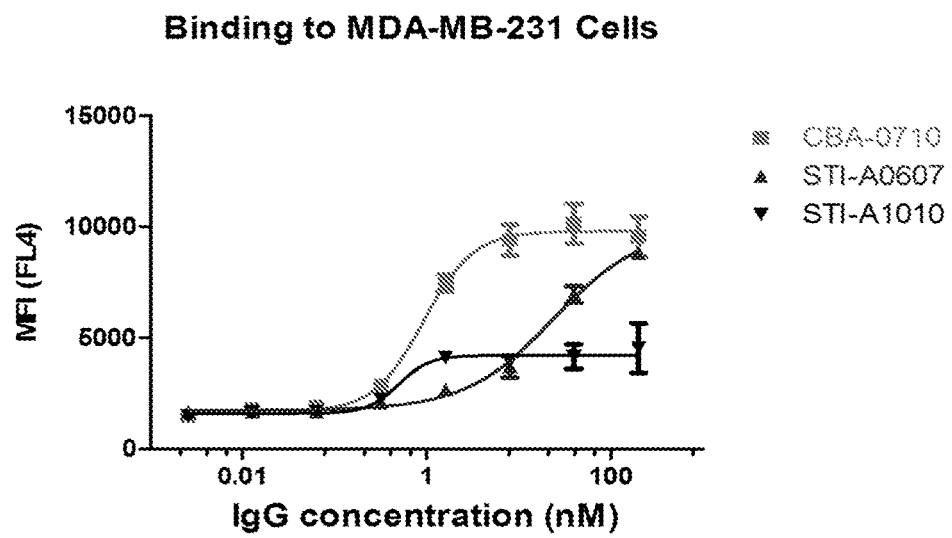
FIG. 15 shows bispecific antibody CBA-0710 binding to triple negative breast cancer cells MDA-MB-231. The cells express both antigen-1 and antigen-2. STI-A0607 is an anti-antigen-1 monoclonal antibody and STI-A1010 is an anti-antigen-2 monoclonal antibody.

The results are illustrated in Table 3 and FIG. 15, and show that the binding of the bispecific antibody to MDA- MB-231 cells was improved compared to the parental types, with a subnanomolar EC50 value similar to the anti-antigen-2 antibody, and a binding intensity as high as with the anti-antigen-1 antibody.

TABLE 3

Binding data of bispecific antibody and parental type antibodies

|  | Bispecific antibody CBA-0710 | Anti-antigen-1 antibody STI-A0607 | Anti-antigen-2 antibody STI-A1010 |
| --- | --- | --- | --- |
| EC50 (nM) | 0.93 | 24.35 | 0.49 |
| Binding intensity (relative fluorescence units) | 8095 | 8239 | 2598 |

Figure 16:
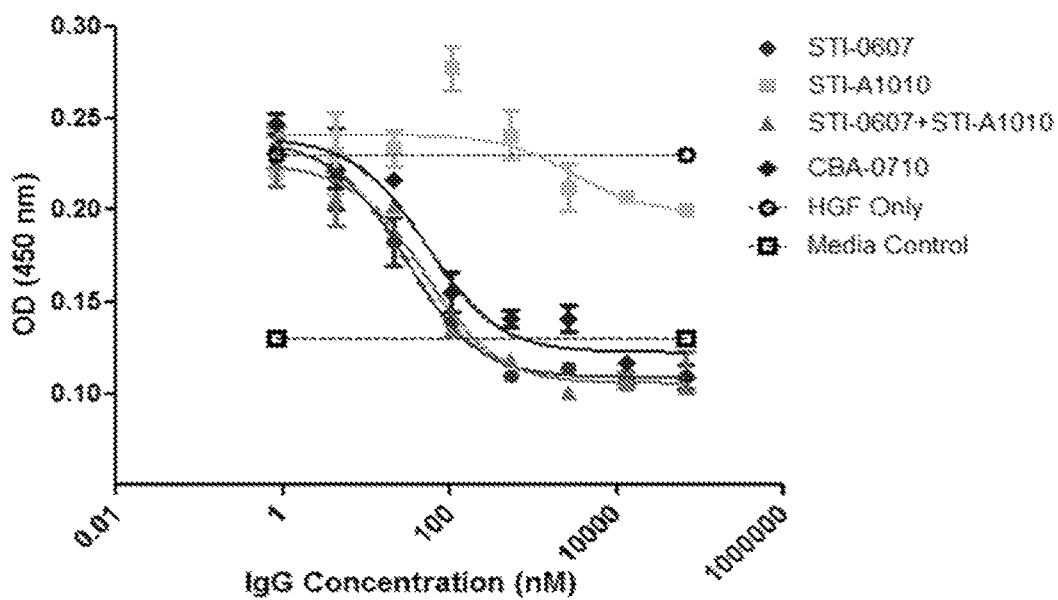
FIG. 16 shows antagonistic activity of bispecific antibody CBA-0710 in triple negative breast cancer cells. STI-A0607 is an anti-antigen-1 monoclonal antibody and STI-A1010 is an anti-antigen 2 monoclonal antibody. HGF is a natural ligand of antigen-1.

There was shown antagonistic activity of bispecific antibody CBA-0710. Specifically, inhibition of c-MET Phosphorylation by bispecific antibody CBA-0710 was run, following PathScan® Phospho-Met (panTyr) Sandwich ELISA Kit #7333 protocol. Briefly, cell lysates were added reconstituted detection antibody and incubated, followed by addition of reconstituted HRP-linker secondary antibody. After wash, TMB substrate was added and incubated. After adding STOP solution, results were read. FIG. 16 shows antagonistic activity of bispecific antibody CBA-0710 in triple negative breast cancer cells. STI-A0607 is an anti-antigen-1 monoclonal antibody and STI-A1010 is an anti-antigen 2 monoclonal antibody. HGF is a natural ligand of antigen-1.

Figure 17:
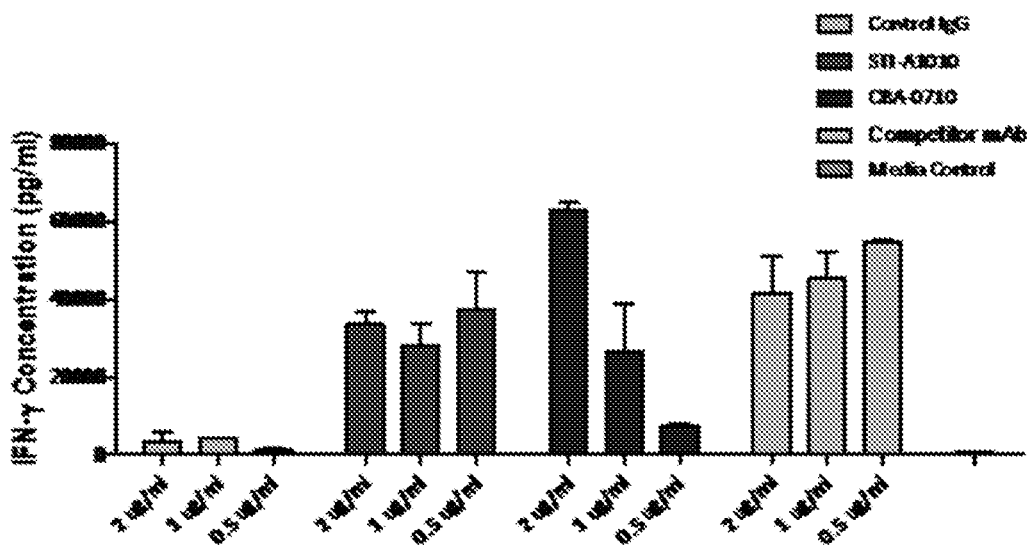
FIG. 17 shows increased IFN-γ release in response to bispecific antibody CBA-0710. STI-A1010 is an anti-antigen-2 (immune checkpoint) monoclonal antibody. Competitor mAb is a humanized anti-antigen-2 (immune checkpoint) monoclonal antibody.
Figure 18:
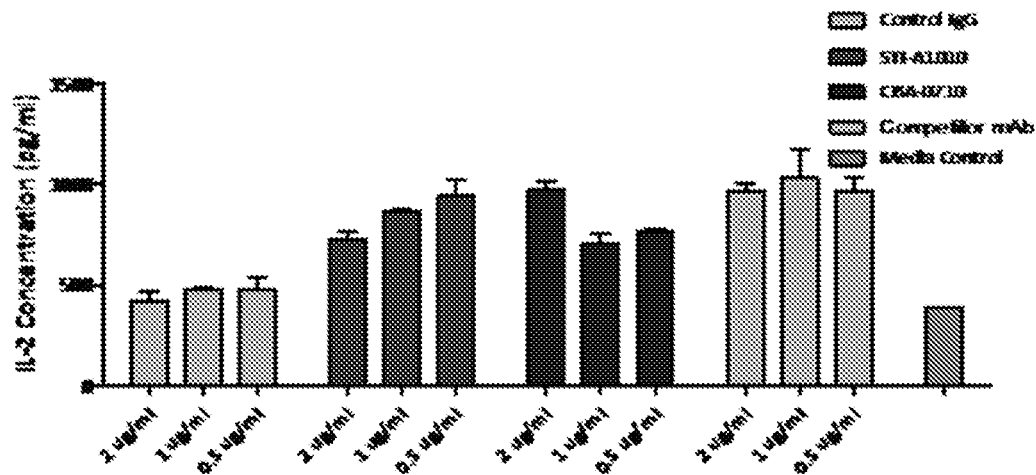
FIG. 18 shows increased IL-2 release in response to bispecific antibody CBA-0710. STI-A1010 is an anti-antigen-2 (immune checkpoint) monoclonal antibody. Competitor mAb is a humanized anti-antigen-2 (immune checkpoint) monoclonal antibody.
Figure 19:
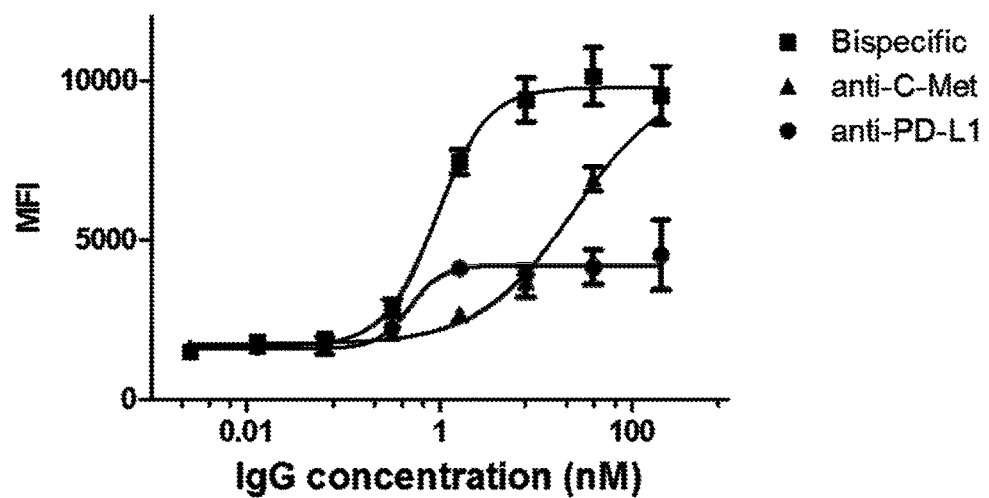
FIG. 19 shows improved efficacy for a chemically locked bispecific antibody composed of A an anti-c-Met antibody and a B an anti-PD-L1 antibody compared to the regular anti-c-Met IgG1 and anti-PD-L1 IgG1 antibodies.

There was immunomodulatory activity of bispecific antibody CBA-0710. To measure the ability of the bispecific antibody CBA-0710 to modulate T cell responsiveness, purified CD4+ cells were cultured with allogeneic dendritic cells, prepared by culturing monocytes in GM-CSF and IL-4 for seven days. Parallel plates were set up to allow collection of supernatants at day 3 and day 5 to measure IL-2 and IFNγ respectively using a commercial ELISA kit. Competitor's humanized anti-antigen-2(immune checkpoint) mAb was produced in-house and used as positive control IgG1 and an unrelated STI human mAb was utilized as negative control IgG antibody. FIG. 17 shows increased IFN-γ release in response to bispecific antibody CBA-0710. STI-A1010 is an anti-antigen-2 (immune checkpoint) monoclonal antibody. Competitor mAb is a humanized anti-antigen-2 (immune checkpoint) monoclonal antibody.

Example 7

Figure 20:
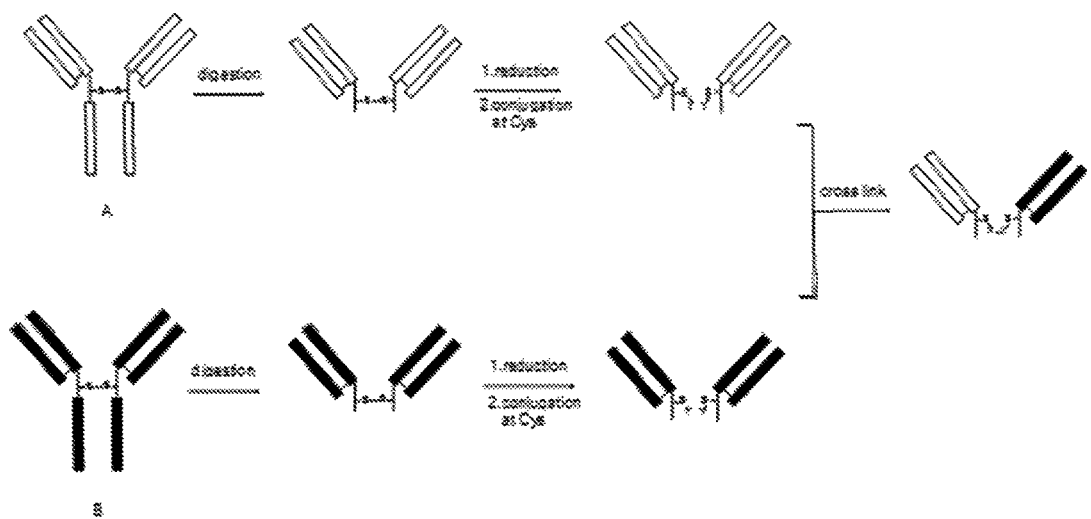
FIG. 20 shows a schematic illustration of generation of bispecific F(ab)'$_2$ via chemical conjugation.
Figure 21:
FIG. 21 shows an SDS_PAGE gel analysis of F(ab)'2 and F(ab)'. Column 1 is antibody A digested with IdeS. Column 2 is antibody B digested with IdeS. Column 3 is antibody A digested and FC removed. Column 4 is antibody B digested and FC removed. Column 5 is antibody A digested and FC removed, reduced with 2MEA and TCEP, and conjugated with DBCO (dibenzocyclooctyl)-maleimide. Column 6 is antibody B digested and FC removed, reduced with 2MEA and TCEP conjugated with Azide-maleimide.
Figure 22:
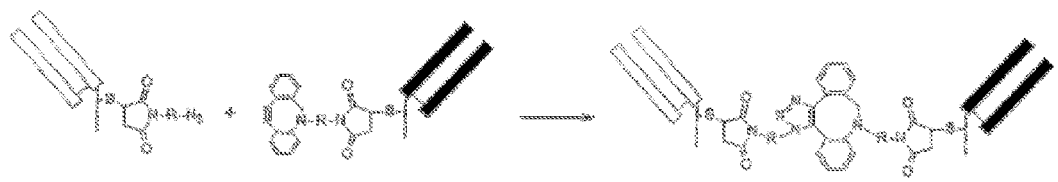
FIG. 22 shows a schematic of a generation of a F(ab)'$_2$ chemically locked bispecific antibody via Click conjugation between two F(ab)' fragments.

This example illustrates a scheme to synthesize the disclosed bispecific antibodies using F(ab)′$_2$ antibodies A' and B'. A bi-specific F(ab)′$_2$ described herein is made up of two F(ab)' fragments chemically linked at the hinge region (FIG. 20). The starting antibodies are either IgG1 or IgG4 isotypes. The starting antibodies contain a modified hinge region wherein a Cys residue was mutated to a Ser residue, leaving only one disulfide at the hinge region. The generation of a bispecific F(ab)′$_2$ chemically-locked bispecific antibody involves four main steps. The first step is removing the Fc fragment. The second step is a selective reduction of antibody A and B respectively. The third step is an introduction of a functional moiety X or Y in the hinge region via a cysteine-based conjugation, leading to a chemically modified antibody fragment A' and B' respectively. In the last step, two antibody fragments are linked together through a chemical ligation between X and Y to form a bispecific F(ab)′$_2$. The scheme for this synthesis is shown in FIG. 21.

Specifically, we performed a process for synthesis of a F(ab)′$_2$ chemically locked bispecific antibody with an IgG1 A antibody with a hinge mutation (SPPC; SEQ ID NO.: 3) and an IgG4 B antibody with a hinge mutation (SPSC; SEQ ID NO.: 4). Using enzyme IdeS which is a digestive enzyme that cleaves IgG only at one specific site below the hinge region, the antibodies (1.5 mg) were added to each tube of IdeS (A0-FR1-008) and incubated in 37° C. overnight in a head to head spinner. The Fc fragment were then remove using protein A purification.

Antibody (1-10 mg) was added to a 15 mL filter centrifuge tube (Millipore, UFC903024) and added an appropriate volume of a 50 mM sodium phosphate, 150 mM NaCl, 5 mM EDTA, pH 7.7 buffer to the 50 mL mark on the tube. The tubes were centrifuged at 3,000 RPM for 20 minutes at 22° C. The antibody was transferred into a 1.5 mL plastic vial and concentration checked using a Nanodrop (Fisher, ND-2000 UV-Vis Spectrophotometer). Final antibody concentrations were up to 10 mg/mL.

Added 1 mL of 50 mM sodium phosphate, 150 mM NaCl, 5 mM EDTA, pH 7.7 buffer to one vial that contained 6 mg of 2-Mercaptoethylamine.HCl (resulted in 50 mM 2-MEA). Added 50 mM 2-MEA to F(ab)′$_2$ final concentration 15 mM, mixed well. Incubated at 37° C. for 15 min. Separated the 2-MEA from the reduced F(ab)′$_2$ using a NAP-5 (GE17-0853-02) desalting column.

A stock solution of 1 mg/mL TCEP ((tris(2-carboxyethyl) phosphine)), Sigma-Aldrich, C4706) in pH 8.0 PBS (1.0 mM DTPA) buffer was prepared. Depending on the number of equivalents and resulting mass of F(ab)′$_2$ recovered after protein A purification, five equivalents of TCEP was added to the desalted F(ab)' shaken well and incubated at room temperature for 5 min.

For DBCO(dibenzocyclooctyl)-maleimide and Azide-maleimide conjugation, a stock solution of DBCO-maleimide (Click Chemistry Tools, A108-100) in DMSO (Sigma-Aldrich, 472301) was prepared and 20 equivalent of DBCO-maleimide in DMSO was added to the F(ab)' (A) sample (without purification of TCEP). Final volume of DMSO in antibody sample was about 5% (v/v). The conjugation reaction was conducted for 2 hour at room temperature under mixing by carousel. The Azide-maleimide (20 equivalents) in DMSO was added to the F(ab)' (B) sample. Final volume of DMSO in antibody sample was about 5% (v/v). The conjugation reaction was conducted for 2 hour at room temperature under mixing by carousel.

For a wash step, each sample was placed into a separate 15 mL filter centrifuge tube (Millipore, UFC903024) and added an appropriate volume of 1×DPBS (Corning, 21-031-CM, no calcium or magnesium) buffer to the 50 mL mark on the tube. The samples were centrifuged at 3,000 RPM for 20 minutes at 22° C. The wash step was repeated once more. After wash, the samples were transferred into separate 1.5 mL plastic vials and placed in refrigerator (5° C.) or was used for click step. Fore F(ab)' fragment analysis an SDS PAGE procedure was used. For each sample to be analyzed, 20 μL at a concentration of 0.6 mg/mL was required. Followed the established protocols for running SDS-PAGE gels (RTP AD001-01 and AD002-01) (FIG. 21).

Figure 23:
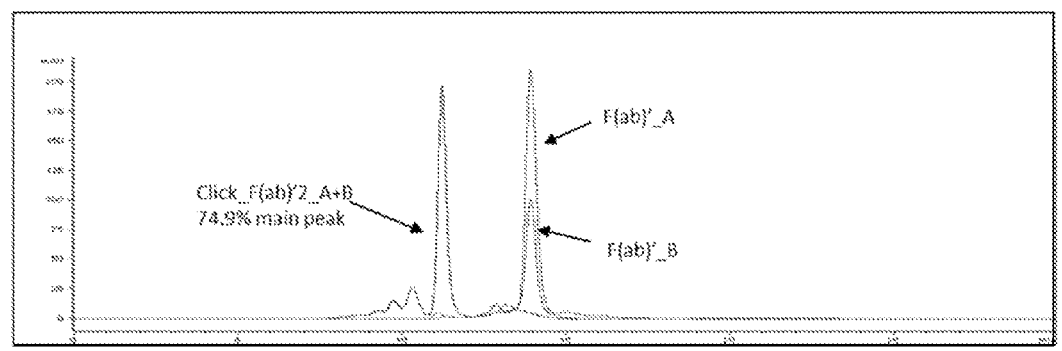
FIG. 23 shows the SEC of Click F(ab)'2 from Example 7 herein.
Figure 24:
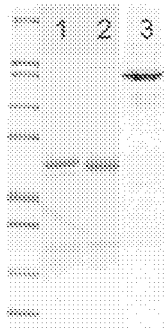
FIG. 24 shows Click bispecific F(ab)'$_2$ fragment analysis SDS PAGE. Column 1 is antibody A digested and FC removed and reduce with 2MEA and TCEP conjugated with DBCO(dibenzocyclooctyl)-maleimide. Column 2 is antibody B digested and FC removed and reduce with 2MEA and TCEP conjugated with Azide-maleimide. Column 3 is Click bispecific F(ab)'$_2$.

The Click reaction scheme between two F(ab)' fragments is shown in FIG. 23. To the F(ab)'-azide fragment (500 μg) in PBS (5.0 mg/mL) was added F(ab)'-DBCO fragment (500 μg) in PBS (5.0 mg/mL). The reaction was conducted for overnight at room temperature under mixing by carousel. The mixture was subject to SEC analysis (FIG. 24).

The biophysical properties of the bispecific antibody made in this example was done using Size-exclusion chromatography (SEC). A size-exclusion chromatography (SEC) Agilent 1200 HPLC using a TSK gel SuperSW3000 column (4.6 mm ID×30 cm, 4 μm) was used to analyze the F(ab)'_A, F(ab)'_B and bispecific Click_F(ab)'$_2$ (FIG. 24). Buffer 0.2 M potassium phosphate, 0.25M KCl, pH 6.2.

Figure 25:
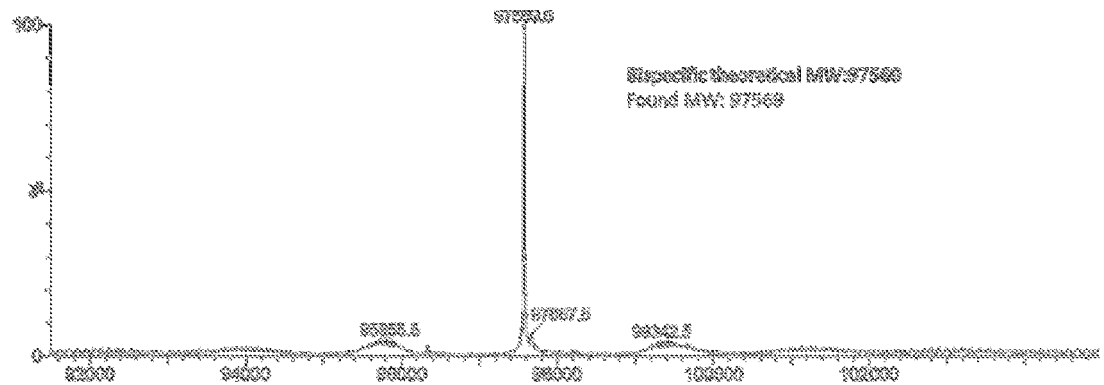
FIG. 25 shows a mass spectrum of Click product showing the mass of bispecific F(ab)'2.
Figure 26:
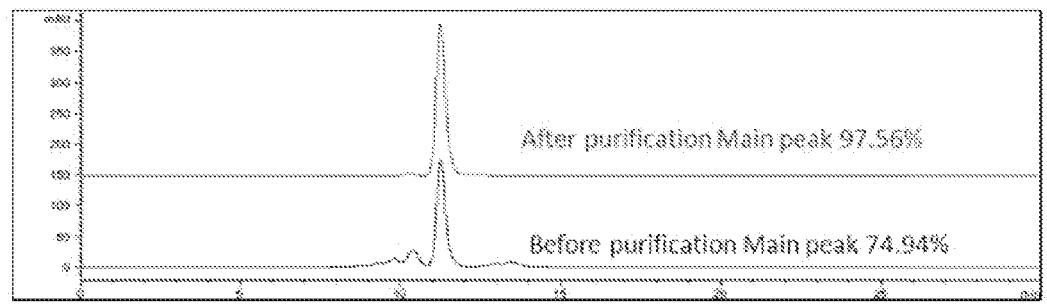
FIG. 26 shows SEC of Click F(ab)'2.

The Bispecific F(ab)'$_2$ was confirmed by mass spectrometry. The bispecific F(ab)'$_2$ analyzed on a Water Xevo G-2 QTOF9 (FIG. 25). Bispecific F(ab)'$_2$ was purified using size-exclusion chromatography (SEC). Size-exclusion chromatography (SEC) Agilent 1200 HPLC using a TSK gel SuperSW3000 column (4.6 mm ID×30 cm, 4 μm) was used to purify the bispecific Click_F(ab)'$_2$ (FIG. 26). Buffer 0.2 M potassium phosphate, 0.25M KCl, pH 6.2.

Figure 27:
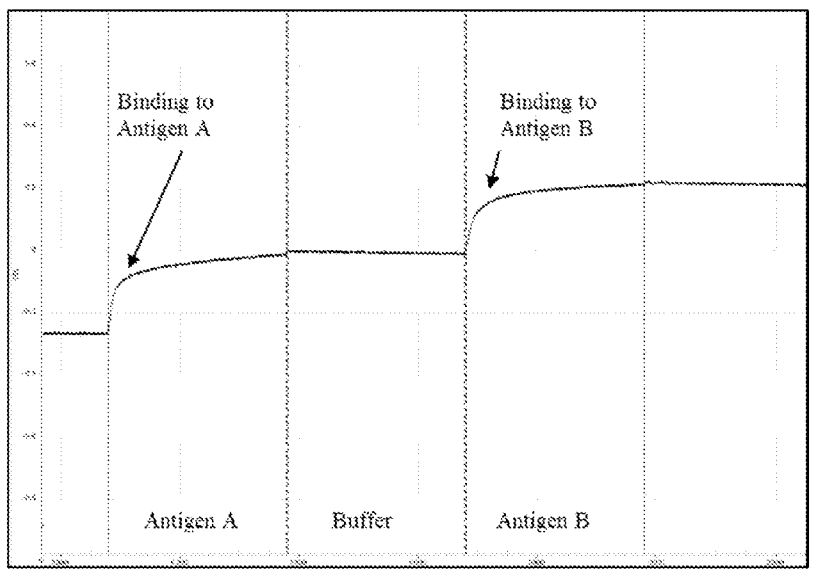
FIG. 27 shows simultaneous binding of bispecific F(ab)'$_2$ to two antigens on Octet Red.
Figure 28:
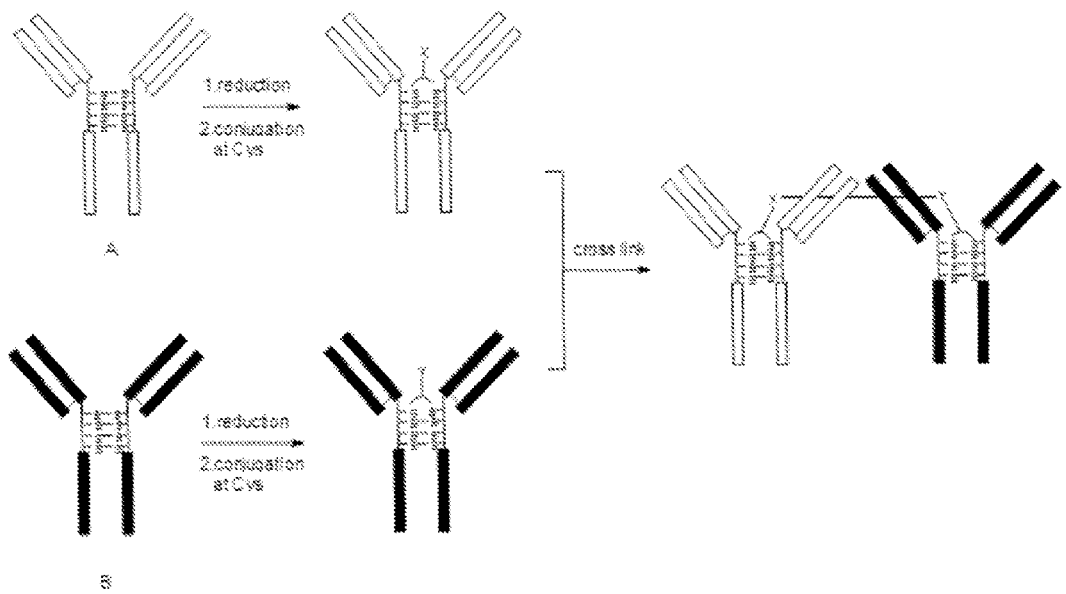
FIG. 28 shows a schematic illustration of generation of bispecific IgG2 via chemical conjugation.

An in vitro affinity measurements was one using Octet Red (FIG. 27). Sensors AR2G were used to measure bispecific F(ab)'$_2$ antigen interactions on the Octet Red (ForteBio, Inc.) In short, the measurement scheme was as follows: 300 seconds baseline; 300 seconds loading of 10 μg/ml bispecific F(ab)'$_2$, 120 seconds baseline; 300 seconds Antigen A; 300 seconds dissociation; 300 seconds Antigen B and 300 seconds dissociation (FIG. 27). Sensor hydration and baseline- and dissociation measurements were performed in PBS.

Example 8

Figure 29:
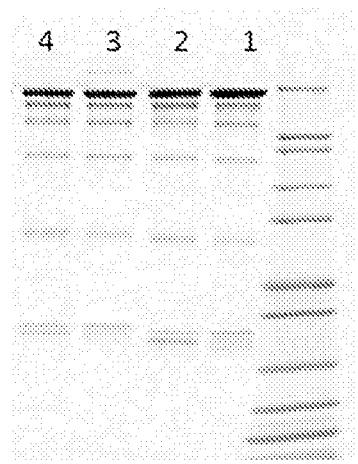
FIG. 29 shows IgG2 fragment analysis SDS PAGE. Column 1 is antibody A. Column 2 is antibody A reduced with TCEP and conjugated with Azide-maleimide. Column 3 is antibody B. Column 4 is antibody B reduced with TCEP and conjugated with Azide-maleimide.

This example illustrates a scheme to synthesize the disclosed bispecific antibodies using IgG2 antibodies A' and B'. A bi-specific IgG2 described herein is made up of two IgG2 fragments chemically linked at the hinge region (FIG. 29). The starting antibodies are IgG2 isotypes. The generation of bi-specific IgG2 involves three main steps. The First step is a reduction of one or two (out of four) disulfide bind in hinge region of IgG2 antibody still maintaining the homodimer structure. The Second step is an introduction of a functional moiety X or Y in the hinge via a cysteine-based conjugation leading to a chemically modified antibody fragment A' and B' respectively. In the last step, two antibody are linked together through a chemical ligation between X and Y to form a bispecific_IgG2.

Specifically, we performed a process for synthesis of an IgG2 chemically locked bispecific antibody. Antibody (1-10 mg) was added to a 15 mL filter centrifuge tube (Millipore, UFC903024) and added an appropriate volume of a 50 mM sodium phosphate, 150 mM NaCl, 5 mM EDTA, pH 7.7 buffer to the 50 mL mark on the tube. The tubes were centrifuged at 3,000 RPM for 20 minutes at 22° C. The antibody was transferred into a 1.5 mL plastic vial and concentration checked using a Nanodrop (Fisher, ND-2000 UV-Vis Spectrophotometer). Final antibody concentrations were up to 10 mg/mL.

A stock solution of 1 mg/mL TCEP ((tris(2-carboxyethyl) phosphine)), Sigma-Aldrich, C4706) in pH 8.0 PBS (2.0 mM DTPA) buffer was prepared. Depending on the number of equivalents and resulting mass of IgG2, two equivalents of TCEP was added to the IgG2 solution, shaken well and incubated at room temperature for 90 min. DBCO(dibenzocyclooctyl)-maleimide and Azide-maleimide For conjugation, a stock solution of DBCO-maleimide (Click Chemistry Tools, A108-100) in DMSO (Sigma-Aldrich, 472301) was prepared and 5 equivalents of DBCO-maleimide in DMSO was added to the IgG2_A sample (without purification of TCEP). Final volume of DMSO in antibody sample was about 5% (v/v). The conjugation reaction was conducted for 1 hour at room temperature under mixing by carousel. Azide-maleimide (5 equivalents) in DMSO was added to the IgG2 (B) sample. Final volume of DMSO in antibody sample was about 5% (v/v). The conjugation reaction was conducted for 1 hour at room temperature under mixing by carousel.

For a wash step, each sample was placed into a separate 15 mL filter centrifuge tube (Millipore, UFC903024) and added an appropriate volume of 1×DPBS (Corning, 21-031-CM, no calcium or magnesium) buffer to the 50 mL mark on the tube. The samples were centrifuged at 3,000 RPM for 20 minutes at 22° C. The wash step was repeated once more. After wash, the samples was transferred into separate 1.5 mL plastic vials and placed in refrigerator (5° C.) or was used for click step.

For each sample to be analyzed, 20 μL at a concentration of 0.6 mg/mL was required. Followed the established protocols for running SDS-PAGE gels (RTP AD001-01 and AD002-01) (FIG. 29).

Figure 30A:
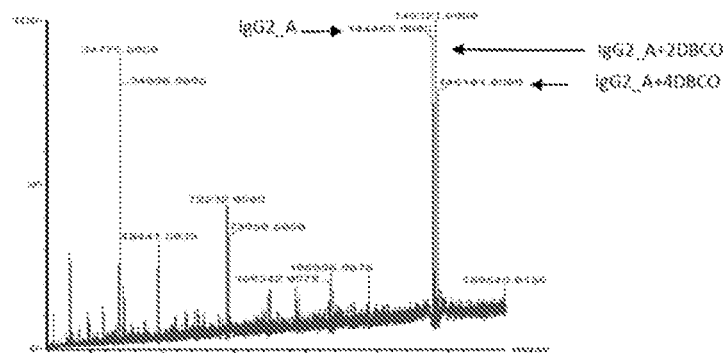
FIG. 30A-C shows mass spectrum showing mass of (FIG. 30A) IgG2_A conjugated with linkers, (FIG. 30B) IgG2_B conjugated with linkers and (FIG. 30C) bispecific-IgG2 formed between IgG2_A and B.
Figure 30B:
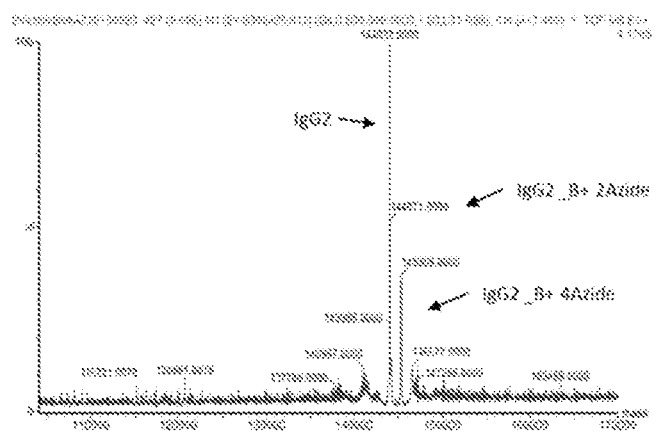
Figure 30C:
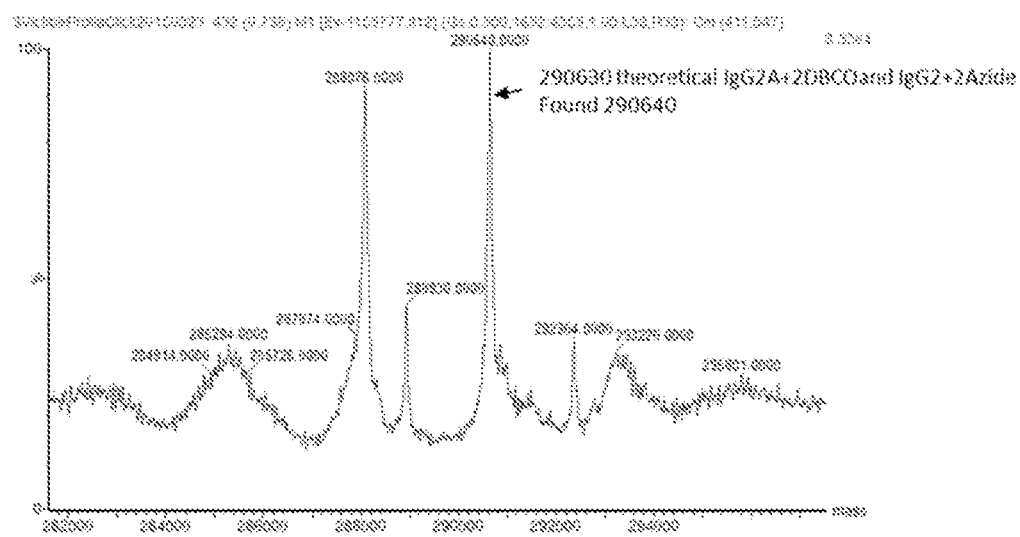

For mass spectrometry, Antibody A was reduced with TCEP and conjugated with DBCO was analyzed on Water Xevo G-2 QTOF. This data suggest conjugation of 2 DBCO (only one disulfide bind reduction) or 4 DBCO (two disulfide bind reduction) to our IgG2 (FIG. 30A-C).

Figure 31:
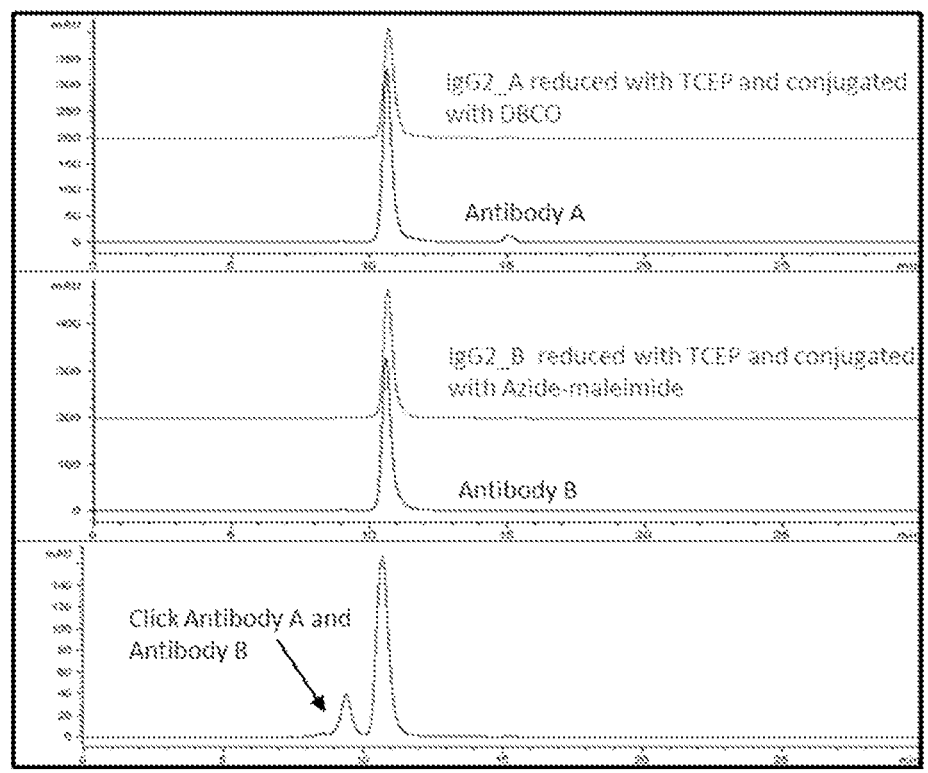
FIG. 31 shows SEC of IgG2_A, IgG2_B and Click product.

The biophysical properties of the bispecific antibody made in this example was done using size-exclusion chromatography (SEC). A size-exclusion chromatography (SEC) Agilent 1200 HPLC using a TSK gel SuperSW3000 column (4.6 mm ID×30 cm, 4 μm) to analyze the bispecific IgG2 (FIG. 31). Buffer 0.2 M potassium phosphate, 0.25M KCl, pH 6.2.

We claim:

1. A bi-specific antibody comprising:
   (a) a first antibody fragment A', comprising a single heavy chain and light chain from an antibody A, wherein the single heavy chain of the first antibody fragment A' has one or two reactive thiol groups in the hinge region, and wherein antibody A is an IgG1, IgG2 or IgG4 class antibody; and
   (b) a second antibody fragment B', comprising a single heavy chain and light chain from an antibody B, wherein the single heavy chain of the second antibody fragment B' has one or two reactive thiol groups in the hinge region, and wherein antibody B is an IgG1, IgG2 or IgG4 class antibody;
   wherein said first antibody fragment A' and second antibody fragment B' are covalently linked through a 1,2,3-triazole formed by a cycloaddition reaction of an azide and an alkyne;
   wherein the azide is attached through a linker to the one or two reactive thiol groups on said first antibody fragment A';
   wherein the alkyne is attached through a linker to the one or two reactive thiol groups on said second antibody fragment B'; and
   wherein the alkyne together with the attached linker has the structure:

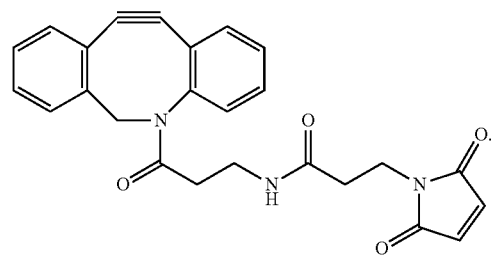 [SMILES: O=C(CCN1C(=O)C=CC1=O)NCCC(=O)N1Cc2ccccc2C#Cc2ccccc21]

2. The bi-specific antibody of claim 1, wherein the azide, together with the attached linker, is selected from:

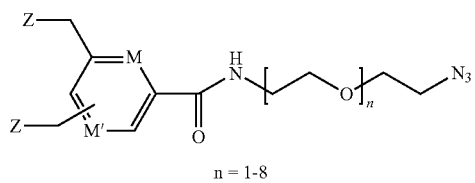

n = 1-8

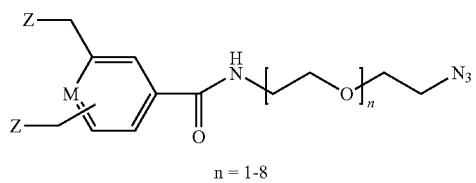

n = 1-8

-continued

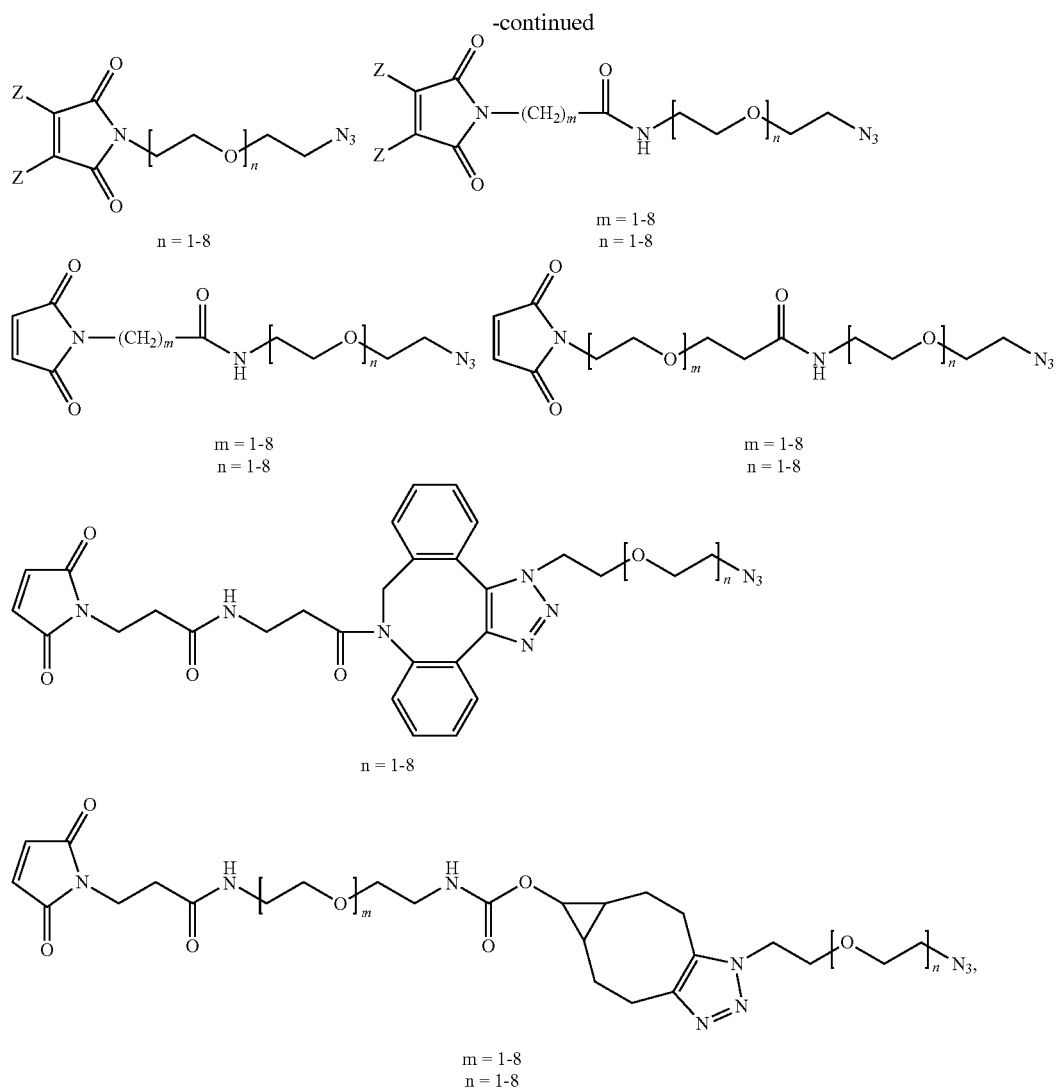

wherein M is N or C;
M' is N or C; and
Z is Br, I or SPh.

3. A pharmaceutical formulation comprising an effective amount of the bispecific antibody of claim 1 in an aqueous solution suitable for human use.

4. The bispecific antibody of claim 1, wherein A' is linked through a reactive thiol group in the hinge region to a moiety having the structure:

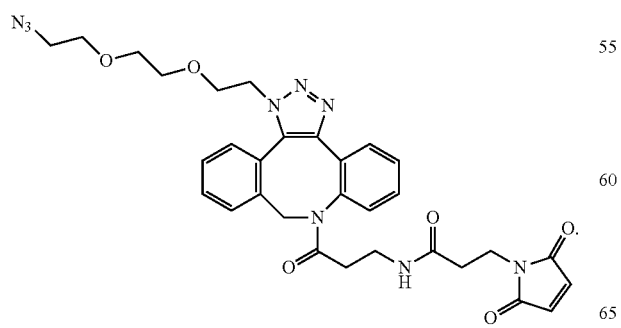

5. The bispecific antibody of claim 1, wherein A' and B' have a hinge residue sequence CPPC (SEQ ID NO:1), or CPSC (SEQ ID NO:2), or SPPC (SEQ ID NO:3), or SPSC (SEQ ID NO:4) (EU-index numbering: residues 226-229; Kabat numbering: residues 239-242).

6. The chemically locked bispecific antibody of claim 1, having the formula:

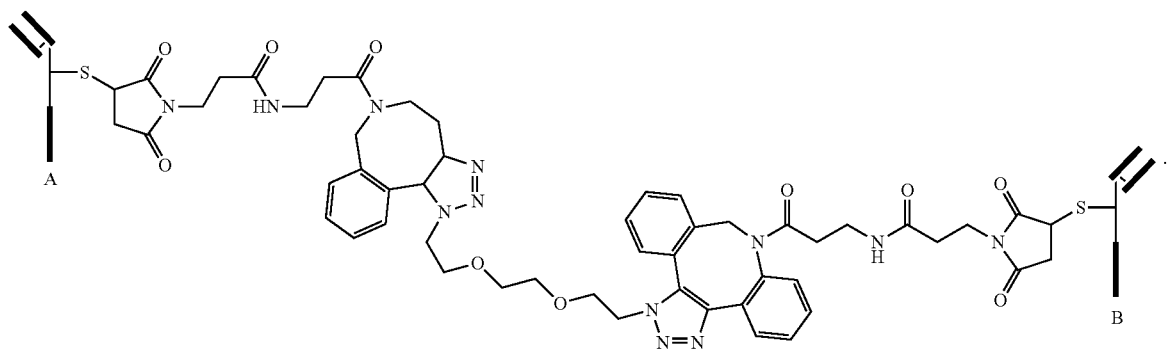
7. The bispecific antibody of claim 1, wherein A and B are IgG1 class antibodies.
8. The bispecific antibody of claim 1, wherein A and B are IgG4 immunoglobulins with hinge mutations SPSC.
9. The bispecific antibody of claim 1, wherein A is an anti-cMet antibody and B is an anti-PD-L1 antibody.
\* \* \* \* \*